(12) United States Patent
Lenser et al.

(10) Patent No.: US 11,642,250 B2
(45) Date of Patent: *May 9, 2023

(54) METHOD AND APPARATUS FOR ASSEMBLING ABSORBENT ARTICLES

(71) Applicant: The Procter & Gamble Company, Cincinnati, OH (US)

(72) Inventors: Todd Douglas Lenser, Liberty Township, OH (US); Urmish Popatlal Dalal, Milford, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 215 days.

This patent is subject to a terminal disclaimer.

(21) Appl. No.: 17/110,351

(22) Filed: Dec. 3, 2020

(65) Prior Publication Data

US 2021/0085532 A1    Mar. 25, 2021

Related U.S. Application Data

(63) Continuation of application No. 16/741,819, filed on Jan. 14, 2020, now Pat. No. 10,959,887, which is a
(Continued)

(51) Int. Cl.
*B29C 65/08* (2006.01)
*A61F 13/15* (2006.01)
(Continued)

(52) U.S. Cl.
CPC .. *A61F 13/15699* (2013.01); *A61F 13/15593* (2013.01); *A61F 13/15601* (2013.01);
(Continued)

(58) Field of Classification Search
CPC ... B29C 65/08; B29C 65/086; B29C 65/7847; B29C 66/344; B29C 66/43;
(Continued)

(56) References Cited

U.S. PATENT DOCUMENTS 3,113,225 A    12/1963  Kleesattel et al.
3,338,992 A     8/1967  Allison
(Continued)

FOREIGN PATENT DOCUMENTS

CN    101170977 A    4/2008
CN    103209828 A    7/2013
(Continued)

OTHER PUBLICATIONS

All Office Actions; U.S. Appl. No. 14/265,629.
(Continued)

*Primary Examiner* — James D Sells
(74) *Attorney, Agent, or Firm* — Sarah M. DeCristofaro; Wednesday G. Shipp

(57) ABSTRACT

The present disclosure relates to methods for assembling elastic laminates that may be used to make absorbent article components. Particular aspects of the present disclosure involve providing a first substrate and a second substrate, the first substrate and the second substrate, each having a width in a cross direction; providing an activated elastic material; elongating the activated elastic material; and ultrasonically bonding the first substrate together with the second substrate with the elongated activated elastic material positioned between the first substrate and the second substrate.

20 Claims, 18 Drawing Sheets

Related U.S. Application Data continuation of application No. 15/674,625, filed on Aug. 11, 2017, now Pat. No. 10,568,776.

(60) Provisional application No. 62/419,515, filed on Nov. 9, 2016, provisional application No. 62/406,025, filed on Oct. 10, 2016, provisional application No. 62/374,010, filed on Aug. 12, 2016.

(51) Int. Cl.

| | | |
|---|---|---|
| *B32B 7/05* | (2019.01) | |
| *A61F 13/49* | (2006.01) | |
| *B29C 55/02* | (2006.01) | |
| *B29C 65/74* | (2006.01) | |
| *B29C 65/00* | (2006.01) | |
| *B32B 5/02* | (2006.01) | |
| *B32B 37/10* | (2006.01) | |
| *B32B 37/14* | (2006.01) | |
| *B32B 38/00* | (2006.01) | |
| *B32B 27/12* | (2006.01) | |
| B32B 15/09 | (2006.01) | |
| B32B 27/30 | (2006.01) | |
| B29C 65/78 | (2006.01) | |
| B32B 7/04 | (2019.01) | |
| B32B 27/06 | (2006.01) | |
| B32B 27/40 | (2006.01) | |
| B32B 5/22 | (2006.01) | |
| B32B 27/34 | (2006.01) | |
| B32B 15/088 | (2006.01) | |
| B32B 27/28 | (2006.01) | |
| B32B 15/095 | (2006.01) | |
| B32B 15/14 | (2006.01) | |
| B32B 15/082 | (2006.01) | |
| B32B 15/04 | (2006.01) | |
| B32B 5/26 | (2006.01) | |
| B29C 55/08 | (2006.01) | |
| B32B 3/08 | (2006.01) | |
| B32B 15/08 | (2006.01) | |
| B32B 37/20 | (2006.01) | |
| B32B 38/18 | (2006.01) | |
| B32B 15/06 | (2006.01) | |
| B32B 25/14 | (2006.01) | |
| B32B 27/36 | (2006.01) | |
| B32B 27/08 | (2006.01) | |
| B29K 21/00 | (2006.01) | |
| B29L 9/00 | (2006.01) | |
| B29L 31/48 | (2006.01) | |

(52) U.S. Cl.
CPC .. *A61F 13/15609* (2013.01); *A61F 13/15674* (2013.01); *A61F 13/15723* (2013.01); *A61F 13/15731* (2013.01); *A61F 13/15739* (2013.01); *A61F 13/15764* (2013.01); *A61F 13/49009* (2013.01); *A61F 13/49012* (2013.01); *A61F 13/49019* (2013.01); *B29C 55/02* (2013.01); *B29C 65/08* (2013.01); *B29C 65/74* (2013.01); *B29C 66/00145* (2013.01); *B29C 66/43* (2013.01); *B29C 66/4722* (2013.01); *B29C 66/83413* (2013.01); *B32B 5/022* (2013.01); *B32B 7/05* (2019.01); *B32B 27/12* (2013.01); *B32B 37/1018* (2013.01); *B32B 37/14* (2013.01); *B32B 38/0012* (2013.01); *A61F 2013/15715* (2013.01); *A61F 2013/15869* (2013.01); *A61F 2013/15926* (2013.01); *A61F 2013/49093* (2013.01); *B29C 55/08* (2013.01); *B29C 65/086* (2013.01); *B29C 65/7847* (2013.01); *B29C 66/1122* (2013.01); *B29C 66/21* (2013.01); *B29C 66/344* (2013.01); *B29C 66/433* (2013.01); *B29C 66/723* (2013.01); *B29C 66/7294* (2013.01); *B29C 66/81469* (2013.01); *B29C 66/83411* (2013.01); *B29C 66/83415* (2013.01); *B29K 2021/003* (2013.01); *B29K 2995/0046* (2013.01); *B29L 2009/00* (2013.01); *B29L 2031/4878* (2013.01); *B32B 3/08* (2013.01); *B32B 5/22* (2013.01); *B32B 5/26* (2013.01); *B32B 7/04* (2013.01); *B32B 15/04* (2013.01); *B32B 15/043* (2013.01); *B32B 15/06* (2013.01); *B32B 15/08* (2013.01); *B32B 15/082* (2013.01); *B32B 15/088* (2013.01); *B32B 15/09* (2013.01); *B32B 15/095* (2013.01); *B32B 15/14* (2013.01); *B32B 25/14* (2013.01); *B32B 27/06* (2013.01); *B32B 27/08* (2013.01); *B32B 27/285* (2013.01); *B32B 27/302* (2013.01); *B32B 27/34* (2013.01); *B32B 27/36* (2013.01); *B32B 27/40* (2013.01); *B32B 37/144* (2013.01); *B32B 37/20* (2013.01); *B32B 38/1858* (2013.01); *B32B 2038/0028* (2013.01); *B32B 2262/0207* (2013.01); *B32B 2262/14* (2013.01); *B32B 2270/00* (2013.01); *B32B 2274/00* (2013.01); *B32B 2307/51* (2013.01); *B32B 2307/718* (2013.01); *B32B 2307/732* (2013.01); *B32B 2555/02* (2013.01); *B32B 2556/00* (2013.01)

(58) Field of Classification Search
CPC .......... B29C 66/4722; B29C 66/83413; B32B 5/022; B32B 7/05; B32B 27/12; B32B 37/1018; B32B 37/14; B32B 38/0012
USPC ....................................................... 156/73.1
See application file for complete search history.

(56) References Cited

U.S. PATENT DOCUMENTS

| | | |
|---|---|---|
| 3,562,041 A | 2/1971 | Robertson |
| 3,566,726 A | 3/1971 | Politis |
| 3,692,613 A | 9/1972 | Pederson |
| 3,733,238 A | 5/1973 | Long et al. |
| 3,802,817 A | 4/1974 | Matsuki |
| 3,848,594 A | 11/1974 | Buell |
| 3,849,241 A | 11/1974 | Butin |
| 3,860,003 A | 1/1975 | Buell |
| 3,911,173 A | 10/1975 | Sprague, Jr. |
| 3,929,135 A | 12/1975 | Thompson |
| 4,116,892 A | 9/1978 | Schwarz |
| 4,324,314 A | 4/1982 | Beach et al. |
| 4,405,297 A | 9/1983 | Appel |
| 4,463,045 A | 7/1984 | Ahr et al. |
| 4,515,595 A | 5/1985 | Kievit |
| 4,573,986 A | 3/1986 | Minetola et al. |
| 4,610,678 A | 9/1986 | Weisman |
| 4,629,643 A | 12/1986 | Curro |
| 4,634,440 A | 1/1987 | Widlund |
| 4,662,875 A | 5/1987 | Hirotsu |
| 4,673,402 A | 6/1987 | Weisman |
| 4,699,622 A | 10/1987 | Toussant |
| 4,710,189 A | 12/1987 | Lash |
| 4,780,352 A | 10/1988 | Palumbo |
| 4,785,996 A | 11/1988 | Ziecker et al. |
| 4,834,735 A | 5/1989 | Alemany |
| 4,834,741 A | 5/1989 | Sabee |
| 4,842,666 A | 6/1989 | Werenicz |
| 4,846,815 A | 7/1989 | Scripps |
| 4,854,984 A | 8/1989 | Ball |
| 4,888,231 A | 12/1989 | Angstadt |

(56) References Cited

U.S. PATENT DOCUMENTS

| | | |
|---|---|---|
| 4,892,536 A | 1/1990 | DesMarais et al. |
| 4,894,060 A | 1/1990 | Nestegard |
| 4,919,738 A | 4/1990 | Ball et al. |
| 4,940,464 A | 7/1990 | Van Gompel et al. |
| 4,946,527 A | 8/1990 | Battrell |
| 4,990,147 A | 2/1991 | Freeland |
| 5,006,394 A | 4/1991 | Baird |
| 5,037,416 A | 8/1991 | Allen |
| 5,092,861 A | 3/1992 | Nomura et al. |
| 5,137,537 A | 8/1992 | Herron |
| 5,143,679 A | 9/1992 | Weber et al. |
| 5,147,345 A | 9/1992 | Lavon |
| 5,149,720 A | 9/1992 | Desmarais |
| 5,151,092 A | 9/1992 | Buell |
| 5,156,793 A | 10/1992 | Buell et al. |
| 5,167,897 A | 12/1992 | Weber et al. |
| 5,221,274 A | 6/1993 | Buell |
| 5,242,436 A | 9/1993 | Weil |
| 5,246,433 A | 9/1993 | Hasse et al. |
| 5,260,345 A | 11/1993 | Desmarais |
| 5,266,392 A | 11/1993 | Land |
| 5,269,775 A | 12/1993 | Freeland |
| 5,342,338 A | 8/1994 | Roe |
| 5,344,691 A | 9/1994 | Hanschen |
| 5,360,420 A | 11/1994 | Cook et al. |
| 5,376,430 A | 12/1994 | Swenson et al. |
| 5,382,400 A | 1/1995 | Pike |
| 5,387,207 A | 2/1995 | Dyer |
| 5,397,316 A | 3/1995 | Young |
| 5,418,045 A | 5/1995 | Pike |
| 5,422,172 A | 6/1995 | Wu |
| 5,433,715 A | 7/1995 | Tanzer et al. |
| 5,518,801 A | 5/1996 | Chappell et al. |
| 5,554,145 A | 9/1996 | Roe |
| 5,569,234 A | 10/1996 | Buell et al. |
| 5,571,096 A | 11/1996 | Dobrin |
| 5,580,411 A | 12/1996 | Nease |
| 5,591,155 A | 1/1997 | Nishikawa |
| 5,599,335 A | 2/1997 | Goldman et al. |
| 5,607,414 A | 3/1997 | Richards et al. |
| 5,607,760 A | 3/1997 | Roe |
| 5,609,587 A | 3/1997 | Roe |
| 5,622,772 A | 4/1997 | Stokes |
| 5,628,097 A | 5/1997 | Benson |
| 5,635,191 A | 6/1997 | Roe |
| 5,643,588 A | 7/1997 | Roe |
| 5,658,639 A | 8/1997 | Curro et al. |
| 5,665,300 A | 9/1997 | Brignola |
| 5,674,216 A | 10/1997 | Buell et al. |
| 5,691,034 A | 11/1997 | Krueger |
| 5,700,254 A | 12/1997 | McDowall et al. |
| 5,702,551 A | 12/1997 | Huber et al. |
| 5,707,468 A | 1/1998 | Arnold |
| 5,817,199 A | 10/1998 | Brennecke et al. |
| 5,827,909 A | 10/1998 | Desmarais |
| 5,865,823 A | 2/1999 | Curro |
| 5,897,545 A | 4/1999 | Kline et al. |
| 5,916,661 A | 6/1999 | Benson et al. |
| 5,957,908 A | 9/1999 | Kline et al. |
| 5,968,025 A | 10/1999 | Roe et al. |
| 5,972,806 A | 10/1999 | Weinberger |
| 5,993,432 A | 11/1999 | Lodge |
| 6,004,306 A | 12/1999 | Robles |
| 6,030,373 A | 2/2000 | Vangompel |
| 6,036,796 A | 3/2000 | Halbert et al. |
| 6,096,668 A | 8/2000 | Abuto |
| 6,107,537 A | 8/2000 | Elder |
| 6,118,041 A | 9/2000 | Roe et al. |
| 6,120,487 A | 9/2000 | Ashton |
| 6,120,489 A | 9/2000 | Johnson et al. |
| 6,123,792 A | 9/2000 | Samida |
| 6,140,551 A | 10/2000 | Niemeyer |
| 6,153,209 A | 11/2000 | Vega et al. |
| 6,169,151 B1 | 1/2001 | Waymouth |
| 6,255,236 B1 | 7/2001 | Cree |
| 6,310,154 B1 | 10/2001 | Babcock |
| 6,369,121 B1 | 4/2002 | Catalfamo |
| 6,410,129 B2 | 6/2002 | Zhang |
| 6,426,444 B2 | 7/2002 | Roe et al. |
| 6,428,526 B1 | 8/2002 | Heindel |
| 6,432,098 B1 | 8/2002 | Kline |
| 6,454,989 B1 | 9/2002 | Neely |
| 6,458,447 B1 | 10/2002 | Cabell |
| 6,465,073 B1 | 10/2002 | Morman |
| 6,472,045 B1 | 10/2002 | Morman |
| 6,472,084 B1 | 10/2002 | Middlesworth et al. |
| 6,475,600 B1 | 11/2002 | Morman |
| 6,498,284 B1 | 12/2002 | Roe |
| 6,508,641 B1 | 1/2003 | Kubik |
| 6,513,221 B2 | 2/2003 | Vogt |
| 6,518,378 B2 | 2/2003 | Waymouth |
| 6,534,149 B1 | 3/2003 | Daley et al. |
| 6,540,854 B2 | 4/2003 | Couillard |
| 6,555,643 B1 | 4/2003 | Rieger |
| 6,559,262 B1 | 5/2003 | Waymouth |
| 6,572,595 B1 | 6/2003 | Klemp |
| 6,572,598 B1 | 6/2003 | Ashton |
| 6,586,652 B1 | 7/2003 | Roe et al. |
| 6,610,390 B1 | 8/2003 | Kauschke |
| 6,617,016 B2 | 9/2003 | Zhang et al. |
| 6,627,564 B1 | 9/2003 | Morman |
| 6,627,787 B1 | 9/2003 | Roe et al. |
| 6,632,386 B2 | 10/2003 | Shelley |
| 6,645,330 B2 | 11/2003 | Pargass et al. |
| 6,645,569 B2 | 11/2003 | Cramer et al. |
| 6,649,001 B2 | 11/2003 | Heden |
| 6,677,258 B2 | 1/2004 | Carroll |
| 6,692,477 B2 | 2/2004 | Gibbs |
| 6,713,159 B1 | 3/2004 | Blenke et al. |
| 6,758,925 B1 | 7/2004 | Stegelmann |
| 6,767,420 B2 | 7/2004 | Stegelmann |
| 6,818,083 B2 | 11/2004 | Mcamish et al. |
| 6,825,393 B2 | 11/2004 | Roe et al. |
| 6,830,800 B2 | 12/2004 | Curro |
| 6,843,134 B2 | 1/2005 | Anderson |
| 6,849,142 B1 | 2/2005 | Goulait |
| 6,861,571 B1 | 3/2005 | Roe et al. |
| 6,863,933 B2 | 3/2005 | Cramer et al. |
| 6,878,433 B2 | 4/2005 | Curro |
| 6,905,488 B2 | 6/2005 | Olson |
| 6,974,514 B2 | 12/2005 | Hamulski |
| 7,056,404 B2 | 6/2006 | McFall et al. |
| 7,062,983 B2 | 6/2006 | Anderson |
| 7,108,759 B2 | 9/2006 | You |
| 7,112,621 B2 | 9/2006 | Rohrbaugh et al. |
| 7,270,861 B2 | 9/2007 | Broering |
| 7,291,239 B2 | 11/2007 | Polanco |
| 7,435,243 B2 | 10/2008 | Miyamoto |
| 7,531,233 B2 | 5/2009 | Kling |
| 7,569,039 B2 | 8/2009 | Matsuda et al. |
| 7,572,249 B2 | 8/2009 | Betts |
| 7,582,075 B2 | 9/2009 | Betts |
| 7,625,363 B2 | 12/2009 | Yoshimasa |
| 7,741,235 B2 | 6/2010 | Hashimoto |
| 7,803,244 B2 | 9/2010 | Siqueira |
| 7,806,883 B2 | 10/2010 | Fossum |
| 7,819,853 B2 | 10/2010 | Desai |
| 7,824,594 B2 | 11/2010 | Qureshi et al. |
| 7,870,651 B2 | 1/2011 | Middlesworth |
| 7,896,641 B2 | 3/2011 | Qureshi et al. |
| 7,917,985 B2 | 4/2011 | Dorsey |
| 7,931,632 B2 | 4/2011 | Betts |
| 7,954,213 B2 | 6/2011 | Mizutani |
| 7,998,127 B2 | 8/2011 | Betts |
| 8,062,279 B2 | 11/2011 | Miyamoto |
| 8,062,572 B2 | 11/2011 | Qureshi et al. |
| 8,092,438 B2 | 1/2012 | Betts |
| 8,118,801 B2 | 2/2012 | Macura et al. |
| 8,158,043 B2 | 4/2012 | Gibson |
| 8,172,971 B2 | 5/2012 | Yamamoto |
| 8,186,296 B2 | 5/2012 | Brown et al. |
| 8,361,913 B2 | 1/2013 | Siqueira |
| 8,450,557 B2 | 5/2013 | Nishitani |
| 8,454,571 B2 | 6/2013 | Rezai |

(56) References Cited

U.S. PATENT DOCUMENTS

| | | |
|---|---|---|
| 8,480,642 B2 | 7/2013 | Betts |
| 8,491,557 B2 | 7/2013 | Kline |
| 8,491,742 B2 | 7/2013 | Waas |
| 8,496,775 B2 | 7/2013 | Deng |
| 8,502,013 B2 | 8/2013 | Zhao |
| 8,518,004 B2 | 8/2013 | Betts |
| 8,585,666 B2 | 11/2013 | Weisman et al. |
| 8,618,350 B2 | 12/2013 | Mansfield |
| 8,679,391 B2 | 3/2014 | Odonnell |
| 8,690,852 B2 | 4/2014 | Macura |
| 8,697,938 B2 | 4/2014 | Roe |
| 8,709,579 B2 | 4/2014 | Hoenigmann |
| 8,728,051 B2 | 5/2014 | Lu |
| 8,741,083 B2 | 6/2014 | Wennerback |
| 8,776,856 B2 | 7/2014 | Yamamoto |
| 8,795,809 B2 | 8/2014 | Mansfield |
| 8,858,523 B2 | 10/2014 | Sauer |
| 8,939,957 B2 | 1/2015 | Raycheck |
| 8,940,116 B2 | 1/2015 | Gilgenbach |
| 9,102,132 B2 | 8/2015 | Wennerbck |
| 9,169,384 B2 | 10/2015 | Autran |
| 9,211,221 B2 | 12/2015 | Macura |
| 9,301,889 B2 | 4/2016 | Miyamoto |
| 9,333,125 B2 | 5/2016 | Kline |
| 9,358,161 B2 | 6/2016 | Lawson |
| 9,434,143 B2 | 9/2016 | Sablone |
| 9,498,941 B2 | 11/2016 | Sablone |
| 9,533,067 B2 | 1/2017 | Schonbeck |
| 9,687,580 B2 | 6/2017 | Schonbeck |
| 9,724,248 B2 | 8/2017 | Hughes |
| 9,821,542 B2 | 11/2017 | Bruce |
| 10,485,713 B2 | 11/2019 | Schonbeck |
| 10,524,964 B2 | 1/2020 | Sauer |
| 10,561,537 B2 | 2/2020 | Lenser et al. |
| 10,568,775 B2 | 2/2020 | Lenser |
| 10,568,776 B2 | 2/2020 | Lenser |
| 10,575,993 B2 | 3/2020 | Lenser |
| 10,588,789 B2 | 3/2020 | Surushe |
| 10,617,573 B2 | 4/2020 | Koshijima |
| 10,799,396 B2 | 10/2020 | Takeuchi |
| 10,959,887 B2 * | 3/2021 | Lenser ............ A61F 13/49019 |
| 10,966,876 B2 | 4/2021 | Lenser et al. |
| 11,071,654 B2 | 7/2021 | Lenser et al. |
| 11,083,633 B2 | 8/2021 | Lenser et al. |
| 11,135,100 B2 | 10/2021 | Schönbeck et al. |
| 11,179,278 B2 | 11/2021 | Schönbeck et al. |
| 11,266,543 B2 | 3/2022 | Lenser et al. |
| 11,331,223 B2 | 5/2022 | Lenser et al. |
| 11,382,798 B2 | 7/2022 | Lenser et al. |
| 2001/0018579 A1 | 8/2001 | Klemp |
| 2001/0024940 A1 | 9/2001 | Cook et al. |
| 2002/0095129 A1 | 7/2002 | Friderich |
| 2002/0188268 A1 | 12/2002 | Kline |
| 2003/0021951 A1 | 1/2003 | Desai |
| 2003/0105446 A1 | 6/2003 | Hutson |
| 2003/0109843 A1 | 6/2003 | Gibbs |
| 2003/0109844 A1 | 6/2003 | Gibbs |
| 2003/0120240 A1 | 6/2003 | Buell |
| 2003/0124310 A1 | 7/2003 | Ellis |
| 2003/0148684 A1 | 8/2003 | Cramer et al. |
| 2003/0181120 A1 | 9/2003 | Wu |
| 2003/0233082 A1 | 12/2003 | Kline et al. |
| 2004/0087235 A1 | 5/2004 | Morman |
| 2004/0091693 A1 | 5/2004 | Thomas |
| 2004/0102125 A1 | 5/2004 | Morman |
| 2004/0112509 A1 | 6/2004 | Morman |
| 2004/0121690 A1 | 6/2004 | Mleziva |
| 2004/0182499 A1 | 9/2004 | Collier |
| 2004/0209042 A1 | 10/2004 | Peacock |
| 2004/0224132 A1 | 11/2004 | Roe |
| 2005/0008839 A1 | 1/2005 | Cramer et al. |
| 2005/0065487 A1 | 3/2005 | Graef et al. |
| 2005/0107764 A1 | 5/2005 | Matsuda et al. |
| 2005/0154362 A1 | 7/2005 | Warren et al. |
| 2005/0222546 A1 | 10/2005 | Vargo |
| 2005/0245162 A1 | 11/2005 | Mccormack |
| 2005/0287892 A1 | 12/2005 | Fouse |
| 2006/0062963 A1 | 3/2006 | Middlesworth |
| 2006/0089616 A1 | 4/2006 | Belau et al. |
| 2006/0135024 A1 | 6/2006 | Thomas |
| 2006/0148361 A1 | 7/2006 | Mccormack |
| 2006/0149209 A1 | 7/2006 | Malchow |
| 2006/0271003 A1 | 11/2006 | Loescher |
| 2006/0287637 A1 | 12/2006 | Lam |
| 2007/0105472 A1 | 5/2007 | Marche |
| 2007/0123124 A1 | 5/2007 | Middlesworth |
| 2007/0141311 A1 | 6/2007 | Mleziva |
| 2007/0142798 A1 | 6/2007 | Goodlander et al. |
| 2007/0142806 A1 | 6/2007 | Roe |
| 2007/0142825 A1 | 6/2007 | Prisco |
| 2007/0143972 A1 | 6/2007 | Kline |
| 2007/0202767 A1 | 8/2007 | Anderson |
| 2007/0219521 A1 | 9/2007 | Hird |
| 2007/0234529 A1 | 10/2007 | Middlesworth |
| 2007/0237924 A1 | 10/2007 | Bruce |
| 2007/0249254 A1 | 10/2007 | Mansfield |
| 2007/0254176 A1 | 11/2007 | Patel |
| 2007/0254547 A1 | 11/2007 | Ducauchuis |
| 2007/0287983 A1 | 12/2007 | Lodge et al. |
| 2008/0003910 A1 | 1/2008 | Hughes |
| 2008/0003911 A1 | 1/2008 | Sabbagh |
| 2008/0045917 A1 | 2/2008 | Autran |
| 2008/0051748 A1 | 2/2008 | Black |
| 2008/0076315 A1 | 3/2008 | Mccormack |
| 2008/0114325 A1 | 5/2008 | Edwall et al. |
| 2008/0119102 A1 | 5/2008 | Hughes |
| 2008/0147031 A1 | 6/2008 | Long et al. |
| 2008/0241476 A1 | 10/2008 | Olguin |
| 2008/0305298 A1 | 12/2008 | Lakshmi |
| 2008/0312622 A1 | 12/2008 | Hundorf |
| 2009/0035527 A1 | 2/2009 | Kobayashi |
| 2009/0069772 A1 | 3/2009 | Sauer |
| 2009/0069778 A1 | 3/2009 | Sauer |
| 2009/0191779 A1 | 7/2009 | Cree |
| 2009/0240222 A1 | 9/2009 | Tomoko |
| 2009/0258210 A1 | 10/2009 | Iyad |
| 2009/0275909 A1 | 11/2009 | Sakaguchi |
| 2009/0292266 A1 | 11/2009 | Bäck |
| 2009/0294044 A1 | 12/2009 | Gill et al. |
| 2009/0299318 A1 | 12/2009 | Faulks |
| 2009/0299322 A1 | 12/2009 | Faulks |
| 2009/0325447 A1 | 12/2009 | Austin |
| 2009/0325448 A1 | 12/2009 | Welch |
| 2009/0326503 A1 | 12/2009 | Lakso |
| 2010/0018579 A1 | 1/2010 | Curran |
| 2010/0062231 A1 | 3/2010 | Abed |
| 2010/0076390 A1 | 3/2010 | Norrby |
| 2010/0090363 A1 | 4/2010 | Larsen |
| 2010/0104830 A1 | 4/2010 | Jaeger |
| 2010/0112313 A1 | 5/2010 | Nakakado |
| 2010/0168704 A1 | 7/2010 | Thomas |
| 2010/0262105 A1 | 10/2010 | Turner |
| 2010/0262107 A1 | 10/2010 | Turner et al. |
| 2010/0268183 A1 | 10/2010 | Een |
| 2010/0280481 A1 | 11/2010 | Kline |
| 2010/0285286 A1 | 11/2010 | Middlesworth |
| 2011/0004176 A1 | 1/2011 | Andersson |
| 2011/0040273 A1 | 2/2011 | Sablone |
| 2011/0046594 A1 | 2/2011 | Sablone |
| 2011/0139657 A1 | 6/2011 | Hird |
| 2011/0139658 A1 | 6/2011 | Hird |
| 2011/0139659 A1 | 6/2011 | Hird |
| 2011/0144610 A1 | 6/2011 | Karlson |
| 2011/0151739 A1 | 6/2011 | Bosler |
| 2011/0152812 A1 | 6/2011 | Hird |
| 2011/0178490 A1 | 7/2011 | Lavon |
| 2011/0196332 A1 | 8/2011 | Cheng |
| 2011/0318987 A1 | 12/2011 | Ooishi |
| 2012/0022490 A1 | 1/2012 | Marche et al. |
| 2012/0045620 A1 | 2/2012 | Oba |
| 2012/0055613 A1 | 3/2012 | Back |
| 2012/0055615 A1 | 3/2012 | Back |
| 2012/0061015 A1 | 3/2012 | Lavon et al. |
| 2012/0061016 A1 | 3/2012 | Lavon et al. |

(56) References Cited

U.S. PATENT DOCUMENTS

| | | |
|---|---|---|
| 2012/0095429 A1 | 4/2012 | Kobayashi et al. |
| 2012/0100351 A1 | 4/2012 | Covelli |
| 2012/0116342 A1 | 5/2012 | Stjernholm |
| 2012/0141742 A1 | 6/2012 | Yamaguchi |
| 2012/0143165 A1 | 6/2012 | Macura et al. |
| 2012/0168063 A1 | 7/2012 | Beuther |
| 2012/0196091 A1 | 8/2012 | Mizutani |
| 2012/0209230 A1 | 8/2012 | Mansfield |
| 2012/0238980 A1 | 9/2012 | Lam |
| 2012/0251771 A1 | 10/2012 | Wilson |
| 2012/0277713 A1 | 11/2012 | Raycheck |
| 2012/0316526 A1 | 12/2012 | Rosati et al. |
| 2012/0321839 A1 | 12/2012 | Uematsu |
| 2013/0017370 A1 | 1/2013 | Yamaguchi |
| 2013/0022784 A1 | 1/2013 | Uematsu |
| 2013/0072887 A1 | 3/2013 | LaVon et al. |
| 2013/0082418 A1 | 4/2013 | Curro et al. |
| 2013/0090623 A1 | 4/2013 | Ohashi |
| 2013/0095279 A1 | 4/2013 | Hauschildt |
| 2013/0144245 A1 | 6/2013 | Roe |
| 2013/0158497 A1 | 6/2013 | Yamaguchi |
| 2013/0164480 A1 | 6/2013 | Sakurai et al. |
| 2013/0165883 A1 | 6/2013 | Kimura |
| 2013/0178815 A1 | 7/2013 | Ohashi |
| 2013/0184665 A1 | 7/2013 | Kato |
| 2013/0211356 A1 | 8/2013 | Nishikawa et al. |
| 2013/0213547 A1 | 8/2013 | Schneider et al. |
| 2013/0218116 A1 | 8/2013 | Schneider et al. |
| 2013/0230700 A1 | 9/2013 | Schoenbeck |
| 2013/0236700 A1 | 9/2013 | Yamanaka |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0280481 A1 | 10/2013 | Mitsuno |
| 2013/0284850 A1 | 10/2013 | Lenser |
| 2013/0306226 A1 | 11/2013 | Zink et al. |
| 2014/0018222 A1 | 1/2014 | Sablone |
| 2014/0018759 A1 | 1/2014 | Jayasinghe et al. |
| 2014/0039434 A1 | 2/2014 | Xu |
| 2014/0041786 A1 | 2/2014 | Henke et al. |
| 2014/0135194 A1 | 5/2014 | Sablone |
| 2014/0148774 A1 | 5/2014 | Brown |
| 2014/0163500 A1 | 6/2014 | Roe |
| 2014/0163506 A1 | 6/2014 | Roe |
| 2014/0163511 A1 | 6/2014 | Roe et al. |
| 2014/0234575 A1 | 8/2014 | Mitsuno et al. |
| 2014/0330232 A1 | 11/2014 | Schönbeck |
| 2014/0367032 A1 | 12/2014 | Homoelle et al. |
| 2014/0377506 A1 | 12/2014 | Eckstein et al. |
| 2014/0377513 A1 | 12/2014 | Galie et al. |
| 2014/0378924 A1 | 12/2014 | Turner |
| 2015/0032078 A1 | 1/2015 | Collins |
| 2015/0038929 A1 | 2/2015 | Van Malderen |
| 2015/0057630 A1 | 2/2015 | Tange |
| 2015/0126955 A1 | 5/2015 | Sauer |
| 2015/0147530 A1 | 5/2015 | Mitsuno |
| 2015/0147539 A1 | 5/2015 | Thomas |
| 2015/0164699 A1 | 6/2015 | Schmitz |
| 2015/0164705 A1 | 6/2015 | Thomas |
| 2015/0173961 A1 | 6/2015 | Powell et al. |
| 2015/0202091 A1 | 7/2015 | Sablone |
| 2015/0297419 A1 | 10/2015 | Nelson |
| 2015/0297421 A1 | 10/2015 | Nelson |
| 2015/0313774 A1 | 11/2015 | Homoelle et al. |
| 2016/0013614 A1 | 1/2016 | Moto |
| 2016/0136014 A1 | 5/2016 | Arora |
| 2016/0167334 A1 | 6/2016 | Arora |
| 2016/0206485 A1 | 7/2016 | Seitz |
| 2016/0270972 A1 | 9/2016 | Surushe |
| 2016/0324697 A1 | 11/2016 | Schoenbeck |
| 2017/0022339 A1 | 1/2017 | Hanschen et al. |
| 2017/0027775 A1 | 2/2017 | Barnes |
| 2017/0056256 A1 | 3/2017 | Smith |
| 2017/0071800 A1 | 3/2017 | Schonbeck |
| 2017/0079851 A1 | 3/2017 | Greening, II |
| 2017/0079854 A1 | 3/2017 | Butler |
| 2017/0087029 A1 | 3/2017 | Nelson et al. |
| 2017/0142806 A1 | 5/2017 | Park |
| 2017/0252229 A1 | 9/2017 | Bonelli |
| 2017/0335498 A1 | 11/2017 | Hansen |
| 2018/0014979 A1 | 1/2018 | Fujita |
| 2018/0015709 A1 | 1/2018 | Takeuchi |
| 2018/0042777 A1 | 2/2018 | Dalal |
| 2018/0042778 A1 | 2/2018 | Lenser et al. |
| 2018/0042779 A1 | 2/2018 | Lenser |
| 2018/0042780 A1 | 2/2018 | Lenser |
| 2018/0042784 A1 | 2/2018 | Koshijima |
| 2018/0042785 A1 | 2/2018 | Dalal et al. |
| 2018/0042786 A1 | 2/2018 | Mueller |
| 2018/0042787 A1 | 2/2018 | Lenser et al. |
| 2018/0271716 A1 | 9/2018 | Dalal |
| 2018/0271717 A1 | 9/2018 | Dria |
| 2018/0281296 A1 | 10/2018 | Uchida |
| 2019/0046363 A1 | 2/2019 | Lenser |
| 2019/0083323 A1 | 3/2019 | Sakai |
| 2019/0110936 A1 | 4/2019 | Becker |
| 2019/0125597 A1 | 5/2019 | Sauer et al. |
| 2020/0046576 A1 | 2/2020 | Schonbeck |
| 2020/0170846 A1 | 6/2020 | Lenser |
| 2020/0179179 A1 | 6/2020 | Lenser |
| 2020/0268563 A1 | 8/2020 | Lenser |
| 2020/0397625 A1 | 12/2020 | Sakai |
| 2021/0000656 A1 | 1/2021 | Greening, II |
| 2021/0186769 A1 | 6/2021 | Lenser et al. |
| 2021/0186770 A1 | 6/2021 | Lenser et al. |
| 2021/0307970 A1 | 10/2021 | Lenser et al. |
| 2021/0330514 A1 | 10/2021 | Lenser et al. |
| 2021/0393453 A1 | 12/2021 | Schönbeck et al. |
| 2022/0233362 A1 | 7/2022 | Lenser et al. |
| 2022/0287887 A1 | 9/2022 | Lenser et al. |

FOREIGN PATENT DOCUMENTS

| | | |
|---|---|---|
| CN | 104582945 A | 4/2015 |
| CN | 104703567 A | 6/2015 |
| CN | 104797228 A | 7/2015 |
| CN | 103434239 B | 11/2015 |
| CN | 204909840 U | 12/2015 |
| CN | 104837455 B | 4/2018 |
| CN | 108601686 A | 9/2018 |
| EP | 1256594 A1 | 11/2002 |
| EP | 1447066 A1 | 8/2004 |
| EP | 2100575 A2 | 9/2009 |
| EP | 1263580 B1 | 9/2010 |
| EP | 1990188 B1 | 10/2012 |
| EP | 2891480 A1 | 7/2015 |
| EP | 2841364 B1 | 8/2016 |
| EP | 3246443 A1 | 11/2017 |
| EP | 2647360 81 | 6/2018 |
| EP | 3251642 B1 | 8/2020 |
| JP | 2004223238 A | 8/2004 |
| JP | 2007521036 A | 8/2007 |
| JP | 2011139843 A | 7/2011 |
| JP | 4934835 B2 | 3/2012 |
| JP | 5036641 B2 | 7/2012 |
| JP | 2012524645 A | 10/2012 |
| JP | 2017065142 A | 4/2017 |
| JP | 6240733 B1 | 11/2017 |
| WO | 9115365 A1 | 10/1991 |
| WO | 9510996 A1 | 4/1995 |
| WO | 95010996 A1 | 4/1995 |
| WO | 9511652 A1 | 5/1995 |
| WO | 9516746 A1 | 6/1995 |
| WO | 9828123 A1 | 7/1998 |
| WO | 2000045763 A | 8/2000 |
| WO | 2000059430 A1 | 10/2000 |
| WO | 0073031 A1 | 12/2000 |
| WO | 2002067809 A2 | 9/2002 |
| WO | 2003007864 A1 | 1/2003 |
| WO | 2004017882 A2 | 3/2004 |
| WO | 2004017885 A1 | 3/2004 |
| WO | 2004060652 A1 | 7/2004 |

(56) References Cited

FOREIGN PATENT DOCUMENTS

| | | | |
|---|---|---|---|
| WO | 2006124337 | A1 | 11/2006 |
| WO | 2006138725 | A2 | 12/2006 |
| WO | 2007036907 | A3 | 4/2007 |
| WO | 2008023291 | A3 | 2/2008 |
| WO | 2008156075 | A1 | 12/2008 |
| WO | 2009082277 | A1 | 7/2009 |
| WO | 2009146307 | A1 | 12/2009 |
| WO | 2010055699 | A1 | 5/2010 |
| WO | 2010118214 | A1 | 10/2010 |
| WO | 2010126415 | A1 | 11/2010 |
| WO | 2011080643 | A2 | 7/2011 |
| WO | 2011125893 | A1 | 10/2011 |
| WO | 2012052172 | A1 | 4/2012 |
| WO | 2012030571 | A3 | 5/2012 |
| WO | 2012112501 | A1 | 8/2012 |
| WO | 2012137553 | A1 | 10/2012 |
| WO | 2012154318 | A1 | 11/2012 |
| WO | 2013018846 | A1 | 2/2013 |
| WO | 2013027390 | A1 | 2/2013 |
| WO | 2013047890 | A1 | 4/2013 |
| WO | 2013132403 | A1 | 9/2013 |
| WO | 2013157365 | A1 | 10/2013 |
| WO | 2013163141 | A1 | 10/2013 |
| WO | 2014011839 | A1 | 1/2014 |
| WO | 2015168032 | A1 | 11/2015 |
| WO | 2015195467 | A1 | 12/2015 |
| WO | 2015195468 | A1 | 12/2015 |
| WO | 2016069269 | A1 | 5/2016 |
| WO | 2016073713 | A1 | 5/2016 |
| WO | 2016109514 | A1 | 7/2016 |
| WO | 2018031841 | A1 | 2/2018 |
| WO | 2018183315 | A1 | 10/2018 |
| WO | 2016121979 | A1 | 1/2019 |
| WO | 2019089689 | A2 | 5/2019 |

OTHER PUBLICATIONS

All Office Actions; U.S. Appl. No. 16/658,225.
Unpublished U.S. Appl. No. 17/102,810, filed Nov. 24, 2020, to Marcus Schönbeck et al.
Unpublished U.S. Appl. No. 17/102,825, filed Nov. 24, 2020, to Marcus Schönbeck et al.
Unpublished U.S. Appl. No. 17/102,833, filed Nov. 24, 2020, to Marcus Schönbeck et al.
All Office Actions; U.S. Appl. No. 17/102,833, filed Nov. 24, 2020.
All Office Actions; U.S. Appl. No. 15/360,289, filed Nov. 23, 2016.
All Office Actions; U.S. Appl. No. 17/102,810, filed Nov. 24, 2020.
All Office Actions; U.S. Appl. No. 17/102,825, filed Nov. 24, 2020.
All Office Actions; U.S. Appl. No. 17/465,170, filed Sep. 2, 2021.
Unpublished U.S. Appl. No. 17/465,170, filed Sep. 2, 2021, to Marcus Schönbeck et al.
All Office Actions, U.S. Appl. No. 15/674,559.
All Office Actions, U.S. Appl. No. 15/674,561.
All Office Actions, U.S. Appl. No. 15/674,563.
All Office Actions, U.S. Appl. No. 15/674,566.
All Office Actions, U.S. Appl. No. 15/674,575.
All Office Actions, U.S. Appl. No. 15/674,596.
All Office Actions, U.S. Appl. No. 15/674,625.
All Office Actions, U.S. Appl. No. 15/937,180.
All Office Actions, U.S. Appl. No. 15/937,235.
All Office Actions, U.S. Appl. No. 16/049,977.
All Office Actions, U.S. Appl. No. 16/741,819.
All Office Actions, U.S. Appl. No. 16/748,885.
Case 14525; PCT International Search Report and Written Opinion, Appl. No. PCT/US2017/046393, dated Sep. 25, 2017, 16 pages.
EP Application No. 17754982.1, Third Party Observation, dated Jun. 17, 2020, 9 pages.
EP Application No. 17764961.3, Third Party Observation, dated Aug. 24, 2020, 6 pages.
Extended European Search Report and Search Opinion; Application No. 20183749.9 dated Nov. 9, 2020; 8 pages.
International Search Report and Written Opinion, Application No. PCT/US2017/046388, dated Sep. 22, 2017, 15 pages.
International Search Report and Written Opinion, Application No. PCT/US2017/046394, dated Sep. 28, 2017, 15 pages.
International Search Report and Written Opinion, Application No. PCT/US2017/046395, dated Sep. 20, 2017, 15 pages.
International Search Report and Written Opinion, Application No. PCT/US2017/046397, dated Sep. 28, 2017, 13 pages.
International Search Report and Written Opinion, Application No. PCT/US2017/046398, dated Sep. 28, 2017, 13 pages.
International Search Report and Written Opinion, Application No. PCT/US2017/049026, dated Oct. 19, 2017, 13 pages.
International Search Report and Written Opinion, Application No. PCT/US2018/024549, dated May 30, 2018, 13 pages.
International Search Report and Written Opinion, Application No. PCT/US2019/024011, dated Jul. 4, 2019, 14 pages.
Internatiional Search Report and Written Opinion; Application No. PCT/US2020/070219; dated Oct. 1, 2020; 14 pages
All Office Actions; U.S. Appl. No. 17/884,913, filed Aug. 10, 2022.
Unpublished U.S. Appl. No. 17/884,913, filed Aug. 10, 2022 to Marcus Schonbeck et al.

\* cited by examiner

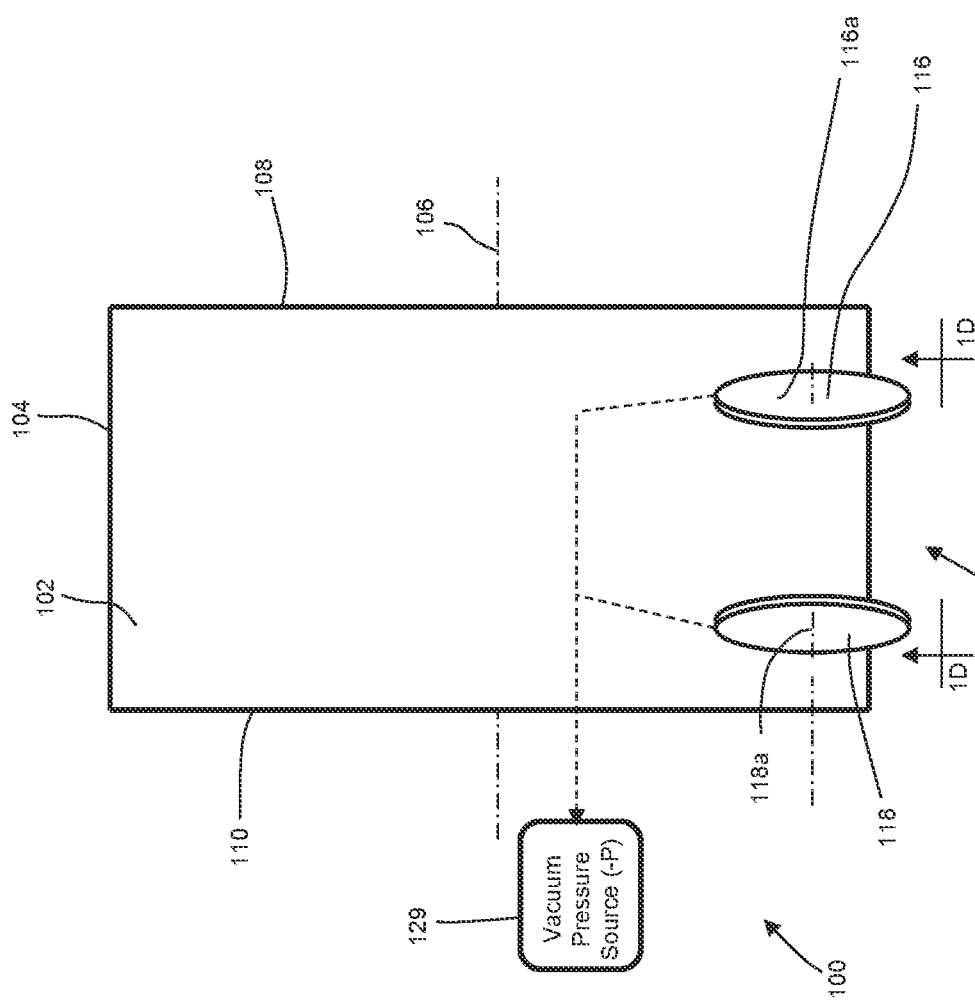

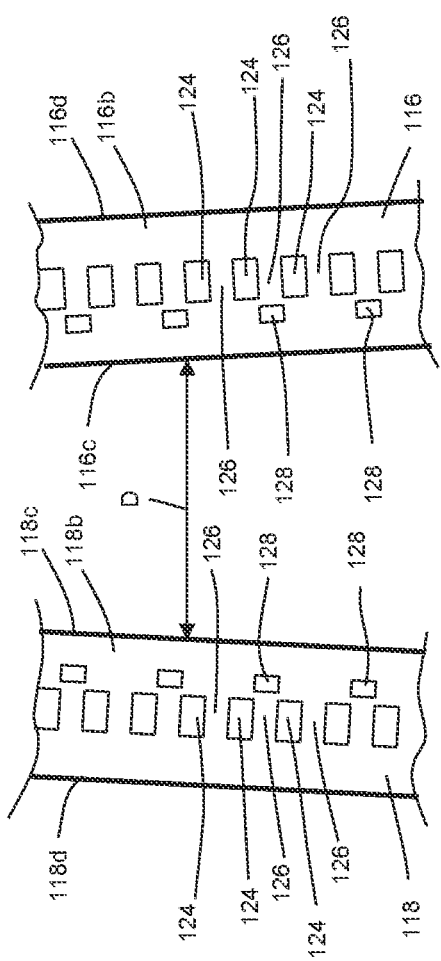
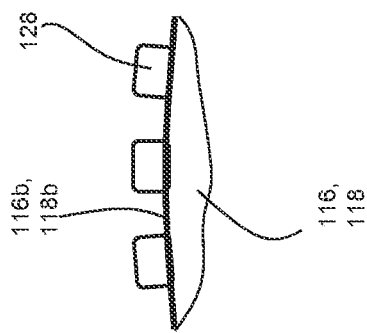
Figure 1D
Figure 1E

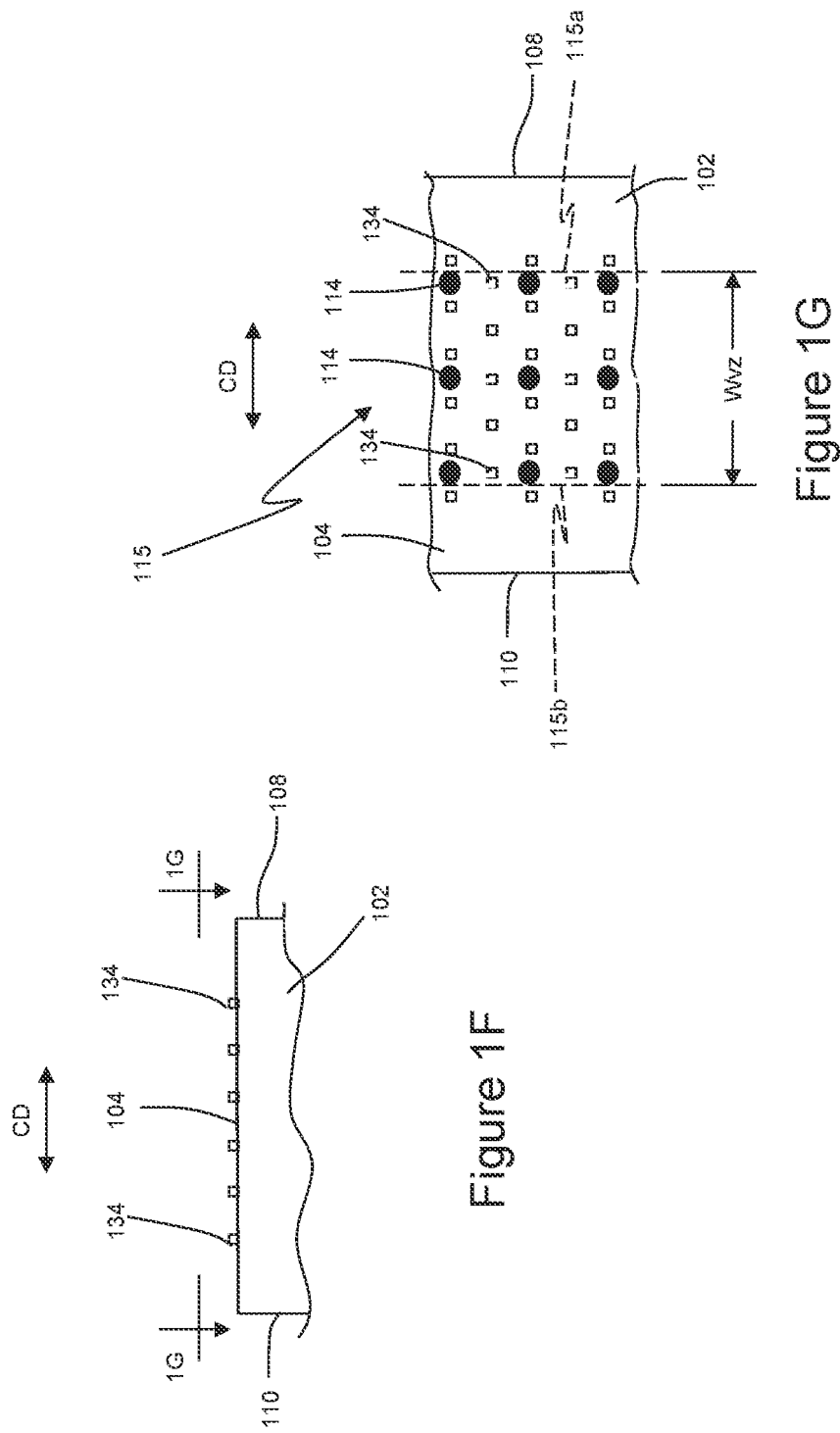

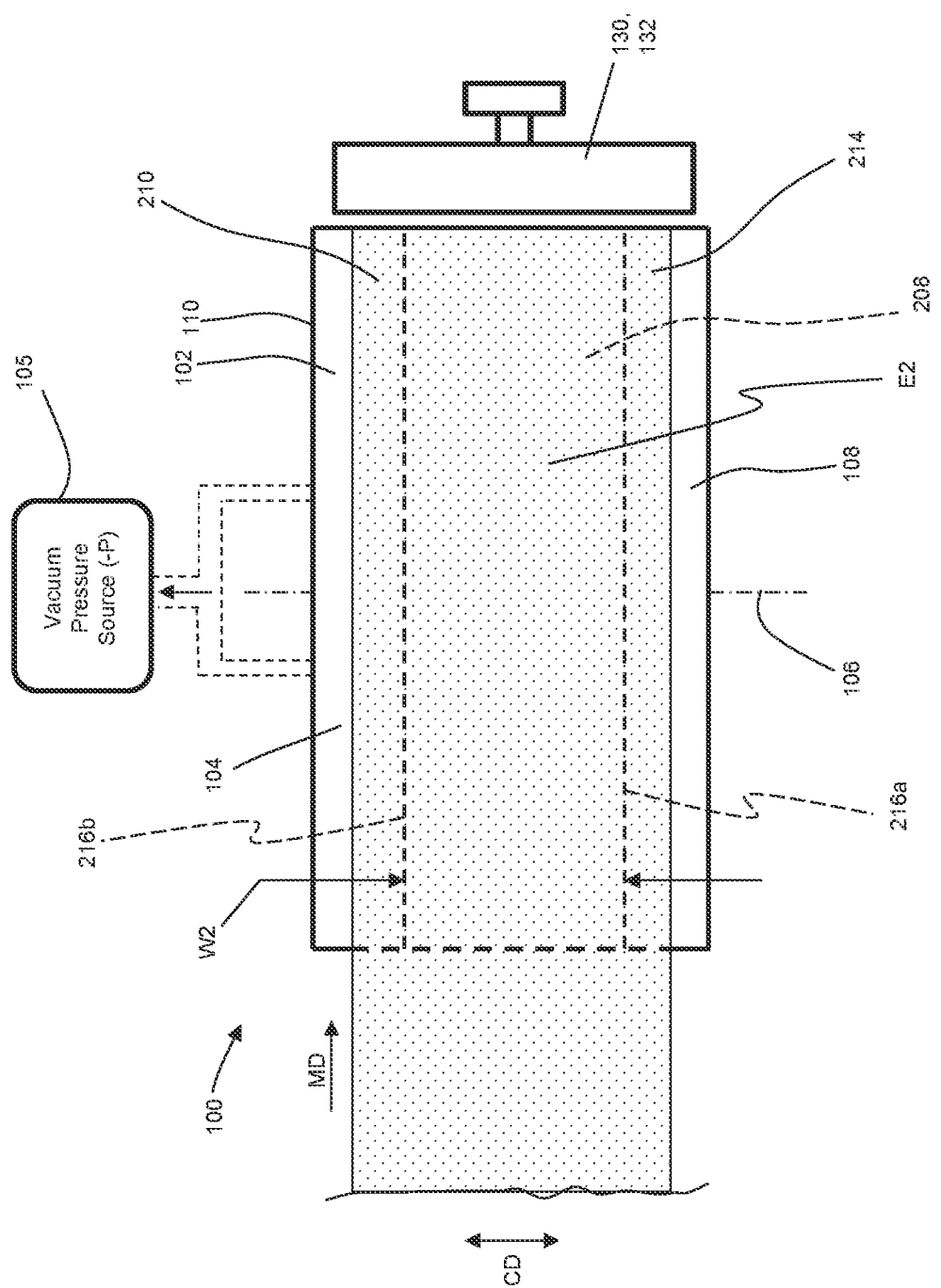

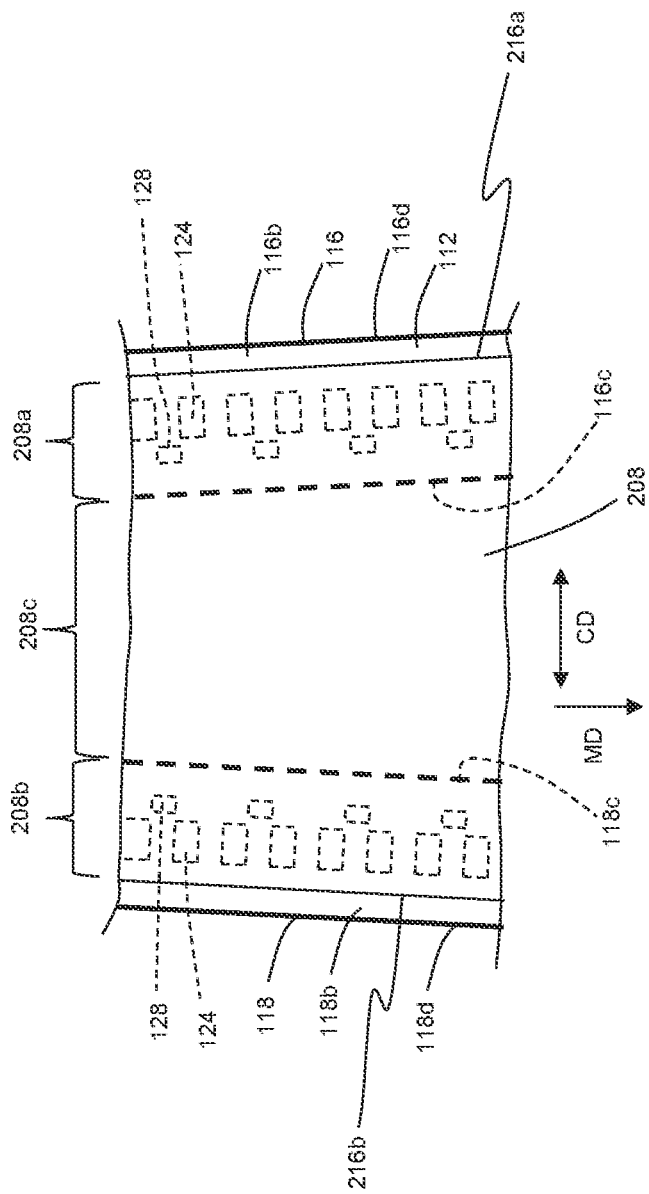

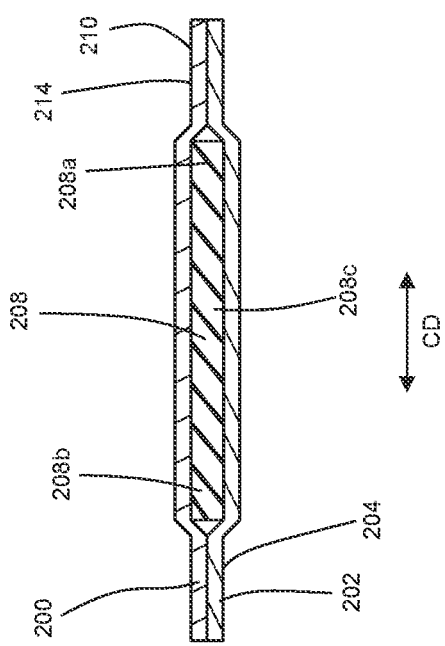
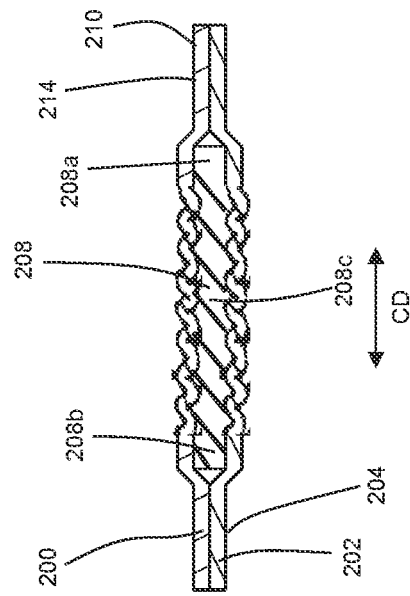

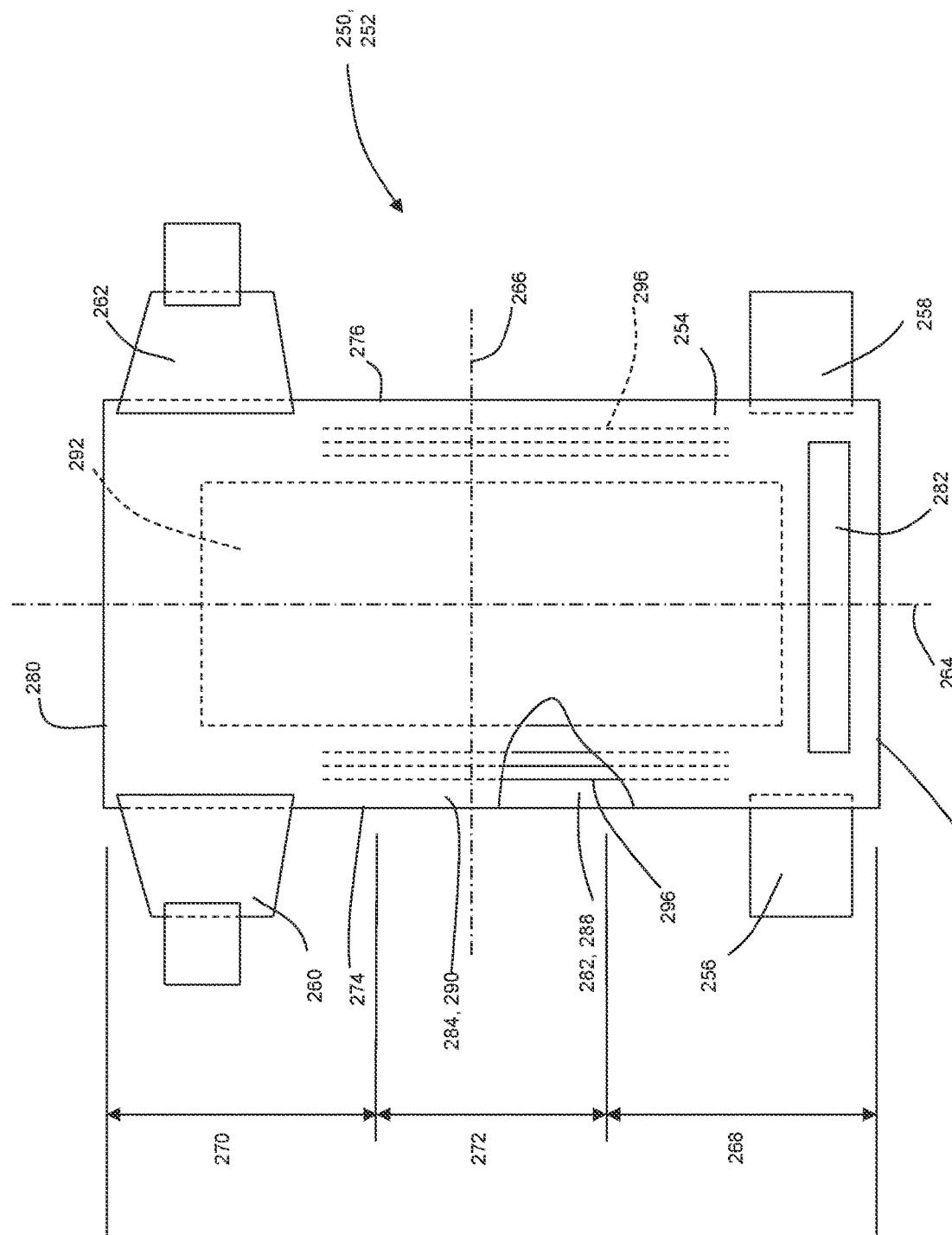

METHOD AND APPARATUS FOR ASSEMBLING ABSORBENT ARTICLES

CROSS REFERENCE TO RELATED APPLICATIONS

This application is a continuation of U.S. patent application Ser. No. 16/741,819, filed on Jan. 14, 2020, which is a continuation of U.S. patent application Ser. No. 15/674,625, filed on Aug. 11, 2017, which claims the benefit of U.S. Provisional Application No. 62/374,010, filed on Aug. 12, 2016; 62/406,025, filed on Oct. 10, 2016; and 62/419,515, filed on Nov. 9, 2016, the entireties of which are all incorporated by reference herein.

FIELD OF THE INVENTION

The present disclosure relates to methods for manufacturing absorbent articles, and more particularly, to apparatuses and methods for assembling elastic laminates for making absorbent article components.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing web or webs. Webs of material and component parts used to manufacture diapers may include: backsheets, topsheets, leg cuffs, waist bands, absorbent core components, front and/or back ears, and fastening components. Once the desired component parts are assembled, the advancing web(s) and component parts are subjected to a final knife cut to separate the web(s) into discrete diapers or other absorbent articles.

Some diaper components, such as leg elastics, barrier leg cuff elastics, stretch side panels, and waist elastics, are constructed from elastic laminates. Such elastic laminates may be assembled in various ways depending on the particular diaper design. For example, some elastic laminates may be constructed from one or more nonwoven substrates bonded to an elastic film. In some configurations, the elastic film may be stretched and then bonded with the nonwoven substrates to form an elastic laminate.

Elastic laminates may be characterized by the force for a given extension when used in a disposable absorbent article. The magnitude of the force required to extend the elastic laminate may vary between the first extension and subsequent extensions. In some configurations, the elastic laminate may include an elastic film that may comprise a base elastic film, such as a styrenic-block copolymer, and surface layers also known as skins. Such skins may help prevent interlayer adhesion when the elastic film is wound into a roll format for shipping and handling. In some configurations, the skins may be a polyolefin, which may be 0.5-5 microns thick. However, the polyolefin skins on the surface of the elastic film may cause the higher initial extension forces for an elastic laminate. Some manufacturers of films may apply processes to help reduce the initial extension force for a given displacement relative to subsequent extensions. For example, some manufactures of films may apply a process, sometimes referred to as "activation," wherein the films are extended or stretched to create a plurality of cracks and tears in the skins at a microscopic scale. In turn, these cracks and tears may help reduce the skin contribution to the extension forces. In some configurations, activation operations are performed separate to the assembly process, such as for example, activating the films offline wherein the films may be stored until needed for production. For example, activation operations may be accomplished during the manufacture of the films, separately from converting lines that are dedicated to manufacturing elastic laminates the may be used in disposable absorbent articles. After manufacturing and activating the films, the films are delivered to the converting lines, such as in a form of continuous films wound onto a roll.

However, performing activation processes during film manufacture may be relatively inflexible and require extra processes and handling by the supplier of such films, which in turn, may add costs. For example, when implemented as an offline process, the tooling may require tight tolerances that are relatively more difficult to achieve when applied to relatively wide films. In addition, films may be plastically deformed by activation processes, such that the width of the activated film once relaxed is larger than the initial width. Such an increase in width may result in increased costs to the end user.

Consequently, it would be beneficial to provide methods and apparatuses for assembling elastic laminates that are configured to perform activation processes that may be performed online during the article assembly process.

SUMMARY OF THE INVENTION

In one form, a method for assembling elastic laminates comprises the steps of: providing a first substrate and a second substrate, the first substrate and the second substrate, each having a width in a cross direction; providing an activated elastic material; elongating the activated elastic material; and ultrasonically bonding the first substrate together with the second substrate with the elongated activated elastic material positioned between the first substrate and the second substrate.

BRIEF DESCRIPTION OF THE DRAWINGS

FIG. 1C is a left side view of the apparatus from FIG. 1B taken along line 1C-1C.

FIG. 1D is a detailed view of a spreader mechanism from FIG. 1C taken along line 1E-1E.

FIG. 1E is a detailed view of radially protruding nubs on an outer rim of a disk.

FIG. 1F is a detailed view of an anvil from FIG. 1B taken along line 1F-1F.

FIG. 1G is a detailed view of the anvil from FIG. 1F taken along line 1G-1G.

FIG. 2C is a top side view of the apparatus from FIG. 2A taken along line 2C-2C.

FIG. 2D is a detailed view of an elastic material advancing on a spreader mechanism from FIG. 2B taken along line 2D-2D.

FIG. 2E is a cross sectional view of the elastic laminate from FIG. 2A taken along line 2E-2E.

FIG. 2F is a cross-sectional view of the elastic laminate from FIG. 2E in a relaxed, contracted condition.

FIG. 5A is a partially cut away plan view of an absorbent article in the form of a taped diaper that may include one or more elastic laminates manipulated during manufacture according to the apparatuses and methods disclosed herein with the portion of the diaper that faces away from a wearer oriented towards the viewer.

DETAILED DESCRIPTION OF THE INVENTION

Figure 1A:
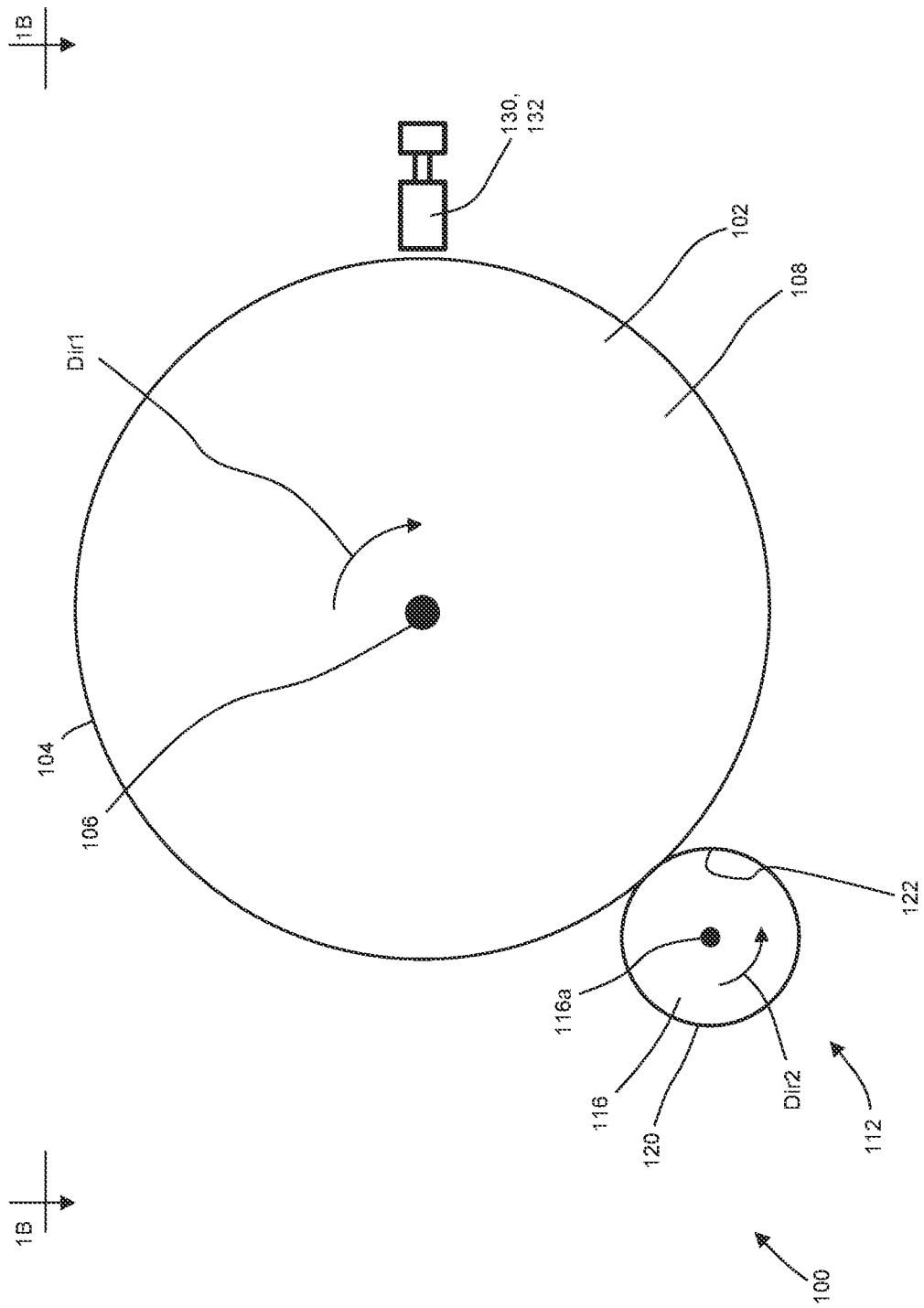
FIG. 1A is a schematic side view of an apparatus for assembling an elastic laminate.

The following term explanations may be useful in understanding the present disclosure:

"Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner). "Diaper" is used herein to refer to an absorbent article generally worn by infants and incontinent persons about the lower torso.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897,545; 5,957,908; 6,120,487; 6,120,489; 7,569,039 and U.S. Patent Publication Nos. 2003/0233082 A; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

An "elastic," "elastomer" or "elastomeric" refers to materials exhibiting elastic properties, which include any material that upon application of a force to its relaxed, initial length can stretch or elongate to an elongated length more than 50% greater than its initial length and will substantially recover back to a length that is about 10% greater than the initial length or less upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

"Consolidation," "consolidating," and "consolidated" refers to a material undergoing a reduction in elongation from a first stretched length to a second stretched length that is less than the first stretched length and greater than zero.

"Relaxed state" defines a length of material when not stretched by an applied force.

In the context of the present description, an elongation of 0% refers to a material in relaxed state having a relaxed length of L, and elongation of 150% represents 2.5x the relaxed length, L, of the material. For example, an elastic film having a relaxed length of 100 millimeters would have a length of 250 millimeters at 150% elongation. And an elastic film having a relaxed length of 100 millimeters would have a length of 180 millimeters at 80% elongation.

The present disclosure relates to apparatuses and methods for manufacturing absorbent articles, and more particularly, apparatuses and methods for assembling elastic laminates that may be used to make absorbent article components. Particular aspects of the present disclosure involve an anvil and a spreader mechanism adjacent the anvil. During the assembly process, a first substrate may be advanced in a machine direction onto the rotating anvil. The spreader mechanism operates to activate an elastic material by stretching the elastic material in the cross direction to a first elongation. The elastic material is then consolidated to a second elongation in the cross direction, wherein the second the elongation is less than the first elongation. The consolidated elastic material is then bonded between a first substrate and a second substrate on the anvil. The elastic material and substrates may be bonded in various ways, such as for example, with an ultrasonic bonding device. In some configurations, the first and second substrates may be nonwovens, and the elastic material may be an elastic film and/or an elastic laminate. As discussed in more detail below, the elastic material may be activated and consolidated before advancing to the anvil. In some configurations, the elastic material may be activated before advancing to the anvil and may be consolidated after advancing onto the anvil. The spreader mechanism and anvil configurations herein enable online activation processes that may be conducted while assembling elastic laminates during an absorbent article assembly processes.

It is to be appreciated that aspects of the methods and apparatuses herein may be configured in various ways. To help provide additional context to a subsequent discussion of the method configurations, the following provides a description of apparatuses that may be configured to operate in accordance with the methods disclosed herein.

Figure 1B:
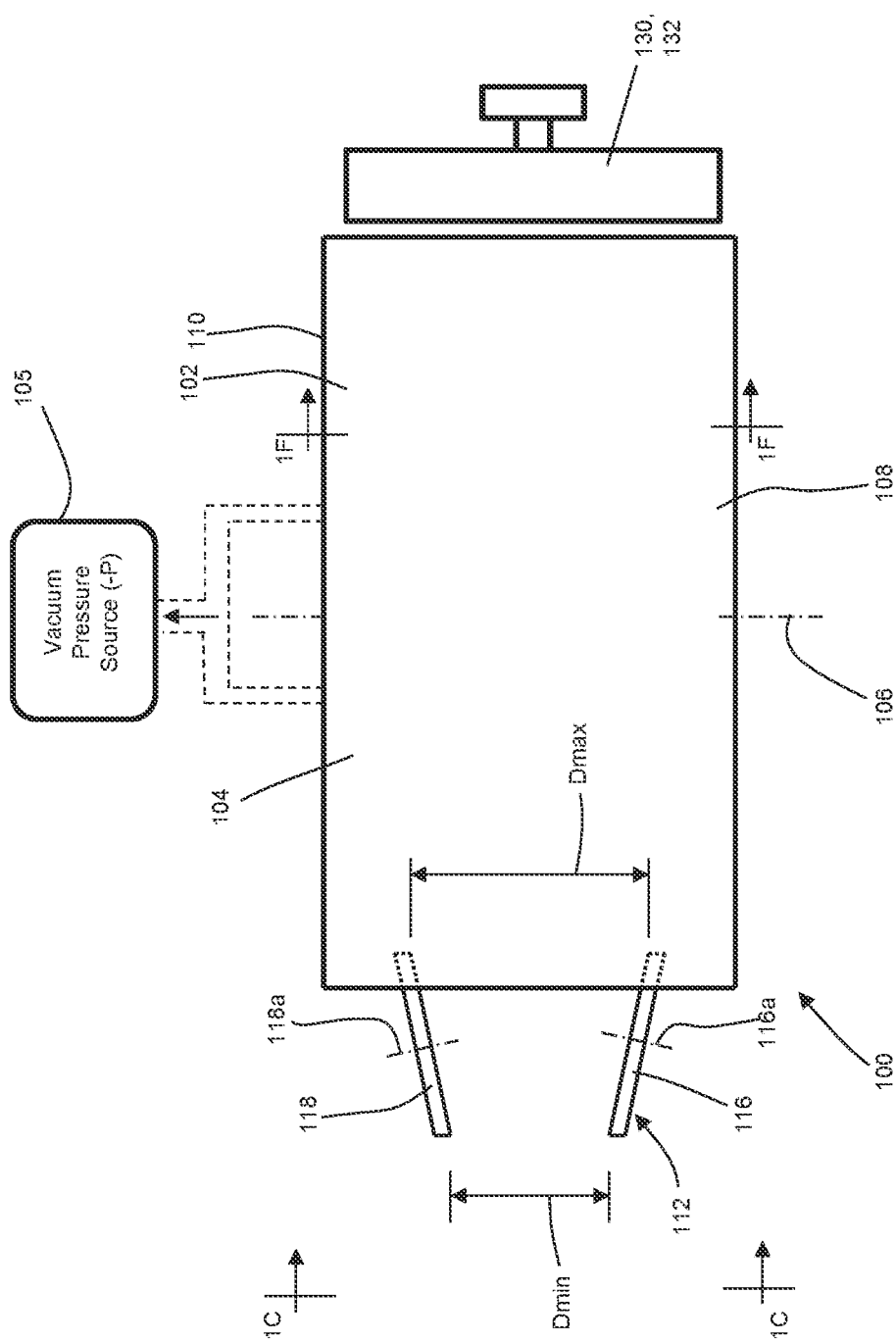
FIG. 1B is a top side view of the apparatus from FIG. 1A taken along line 1B-1B.

FIGS. 1A-1C show schematic side views of an apparatus 100 configured to assemble elastic laminates. As shown in FIGS. 1A-1C, the apparatus includes an anvil 102 having a cylindrically-shaped outer circumferential surface 104 and adapted to rotate in a first direction Dir1 about a first axis of rotation 106. Although the first direction Dir1 is depicted in FIG. 1A as clockwise, it is to be appreciated that the anvil 100 may be configured to rotate such that the first direction Dir1 is counterclockwise. The anvil roll 100 may extend axially for a length between a first end 108 and a second end 110. As discussed in more detail below, substrates and elastic materials may be combined on the rotating anvil 102 to form an elastic laminate. It is to be appreciated that the substrates and elastic materials may be configured in various ways. For example, the substrates may be configured as nonwovens, and the elastic materials may be configured as elastic films and/or elastic laminates.

As shown in FIG. 1B, the anvil 102, and more particularly, the outer circumferential surface 104 may also be fluidly connected with a vacuum pressure source 105. As such, vacuum air pressure may be used to help hold the substrates and elastic materials onto the outer circumferential surface 104 of the anvil 102 during operation. For example, as shown in FIG. 1G, the outer circumferential surface 104 of the anvil roll 102 may include a plurality of apertures 114 fluidly connected with the vacuum pressure source 105. In turn, the apertures 114 may define a vacuum zone 115 extending axially or in the cross direction CD for a width, Wvz. For the purposes of clarity, dashed lines 115a, 115b are shown in FIG. 1G to represent example boundaries of the vacuum zone 115.

As mentioned above, elastic materials, such as elastic films, may include a base elastic film and surface layers also known as skins. During activation, the films may be extended or stretched to create a plurality of cracks and tears in the skins at a microscopic scale, wherein such cracks and tears may help reduce the skin contribution to the extension forces of the elastic film. With continued reference to FIGS. 1A-1C, the apparatus 100 may also include a spreader mechanism 112. As discussed in more detail below, the spreader mechanism 112 may operate to activate the elastic material by stretching the elastic material in a cross direction CD to a first elongation during the elastic laminate assembly process. The stretched elastic material is then consolidated to a second elongation, wherein the second elongation is less than the first elongation. The elastic material is advanced from the spreader mechanism 112 onto a substrate on the rotating anvil 102. In some configurations, the spreader mechanism 112 may be configured to both activate and consolidate the elastic material. In some configurations, the elastic material may be consolidated downstream of the spreader mechanism. It is to be appreciated that the apparatus 100 may include more than one spreader mechanisms configured in various ways, such as disclosed for example in U.S. Patent Application Nos. 62/374,010; 62/406,025; and 62/419,515.

As shown in FIGS. 1A-1E, the spreader mechanism 112 may be configured with canted disks. For example, the spreader mechanism 112 may include a first disk 116 and a second disk 118, wherein the first disk 116 is displaced from the second disk 118 along the axis of rotation 106. The first disk 116 is adapted to rotate about an axis of rotation 116a and the second disk 118 is adapted to rotate about an axis of rotation 118a, wherein the first and second disks 116, 118 rotate in a second direction Dir2 that is opposite the first direction Dir1. Although the second direction Dir2 is depicted in FIG. 1A as counterclockwise, it is to be appreciated that the disks 116, 118 may be configured to rotate such that the second direction Dir2 is clockwise. In addition, the first disk 116 includes an outer rim 116b extending axially between an inner edge 116c and an outer edge 116d, and the second disk 118 includes an outer rim 118b extending axially between an inner edge 118c and an outer edge 118d.

As shown in FIGS. 1A-1D, the first disk 116 and the second disk 118 are canted relative to each other such that the outer rims 116b, 118b are separated from each other by a distance D that increases from a minimum distance Dmin at a first location 120 to a maximum distance Dmax at a second location 122. As discussed below, an elastic material, such as an elastic film, may be advanced in a machine direction MD onto the outer rims 116b, 118b during operation. Because the first and second disks 116, 118 are canted, rotation of the disks 116, 118 causes the rims 116b, 118b to pull on edge regions of the elastic material and activate the elastic material by stretching the elastic material in a cross direction CD. The disks 116, 118 may also be configured to help grip opposing edge regions of the elastic material during operation. For example, with particular reference to FIGS. 1D and 1E, the first disk 116 and the second disk 118 may each include a channel 124 extending radially inward from the rims 116b, 118b. In turn, the channels 124 may be fluidly connected with a vacuum pressure source 129. As such, vacuum air pressure may be used to help hold the elastic material onto the rims 116b, 118b during operation. The disks 116, 118 may also include support members 126 extending across the channels 124 to the help prevent the elastic material from being drawn into the channels 124 by the vacuum air pressure. As shown in FIGS. 1D and 1E, the disks 116, 118 may also include nubs 128 that protrude radially outward from the rims 116b, 118b. As such, the nubs 128 may also act to help prevent the edge regions of the elastic material from sliding along the rims 116b, 118b while stretching the elastic material. It is to be appreciated that additional nubs 128 may be positioned inboard or outboard of the channels 124. In addition, nubs 128 may also be positioned on the support members 126.

As mentioned above, stretched elastic materials and substrates are combined on the anvil 102. The combined substrates and elastic materials may then be ultrasonically bonded together on the anvil 102 to form elastic laminates. As shown in FIGS. 1A and 1B, the apparatus 100 may include one or more ultrasonic mechanisms 130 adjacent the anvil 102. It is to be appreciated that the ultrasonic mechanism 130 may include a horn 132 and may be configured to impart ultrasonic energy to the combined substrates and elastic materials on the anvil 102. As shown in FIGS. 1F and 1G, the anvil roll 102 may include a plurality of pattern elements 134 extending radially outward from the outer circumferential surface 104 of the anvil 102. As such, the ultrasonic mechanism may apply energy to the horn 132 to create resonance of the horn at frequencies and amplitudes so the horn 132 vibrates rapidly in a direction generally perpendicular to the substrates and elastic materials being advanced past the horn 132 on the rotating anvil 102. Vibration of the horn 132 generates heat to melt and bond the substrates and elastic material together in areas supported by the pattern elements 134 on the anvil 102. It is to be appreciated that aspects of the ultrasonic mechanisms may be configured in various ways, such as disclosed for example in U.S. Pat. Nos. 3,113,225; 3,562,041; 3,733,238; 6,036,796; 6,508,641; and 6,645,330. In some configurations, the ultrasonic mechanism may be configured as a linear oscillating type sonotrode, such as for example, available from Herrmann Ultrasonic, Inc. In some configurations, the sonotrode may include a plurality of sonotrodes nested together in the cross direction CD.

As previously mentioned, the apparatus 100 described above with reference to FIGS. 1A-1G may operate to assemble elastic laminates configured in various ways. For example, FIGS. 2A-2D show various schematic views of the apparatus 100 operating to assemble an elastic laminate 200.

Figure 2A:
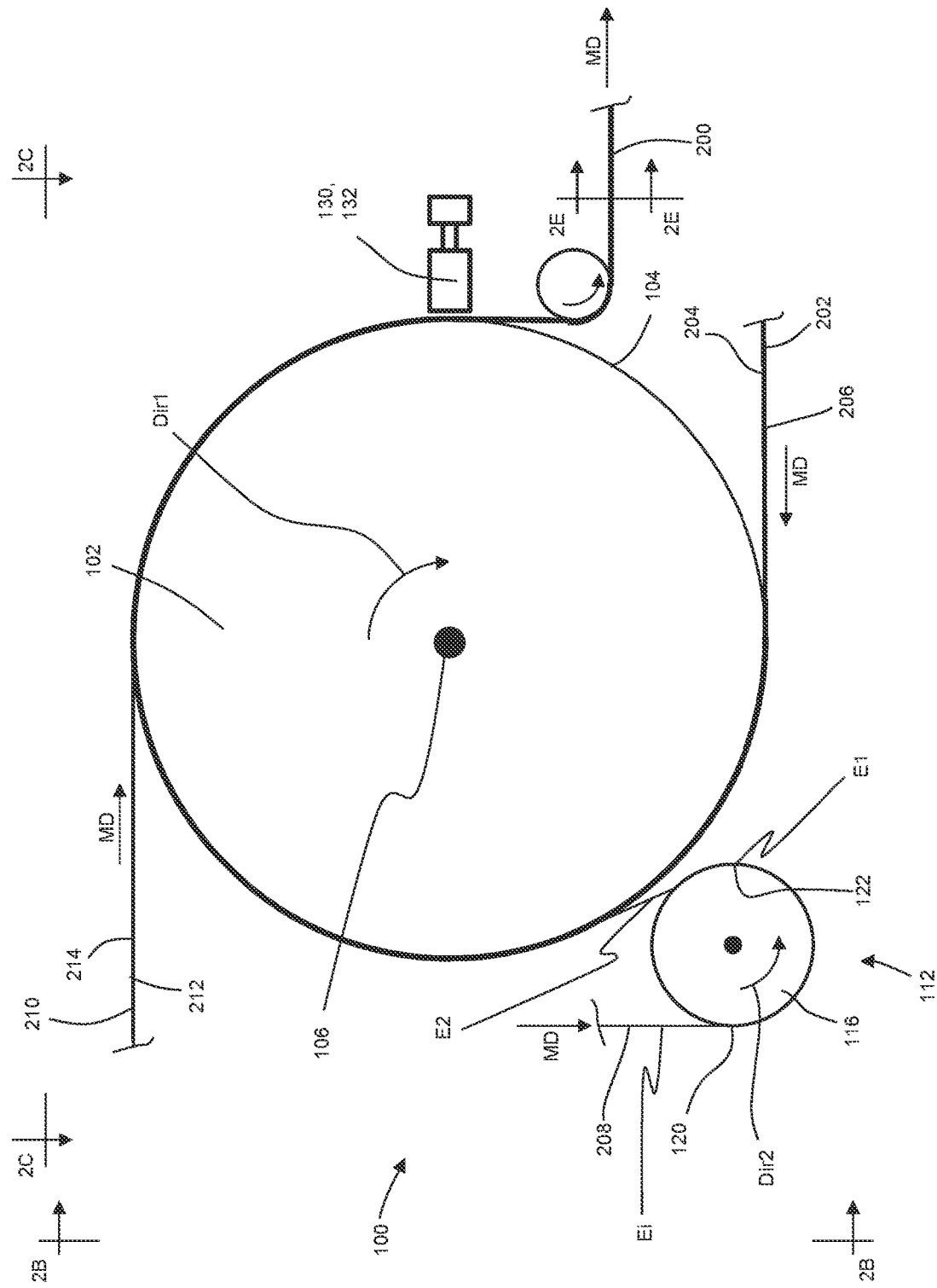
FIG. 2A is a schematic side view of an apparatus operating to assemble an elastic laminate.
Figure 2B:
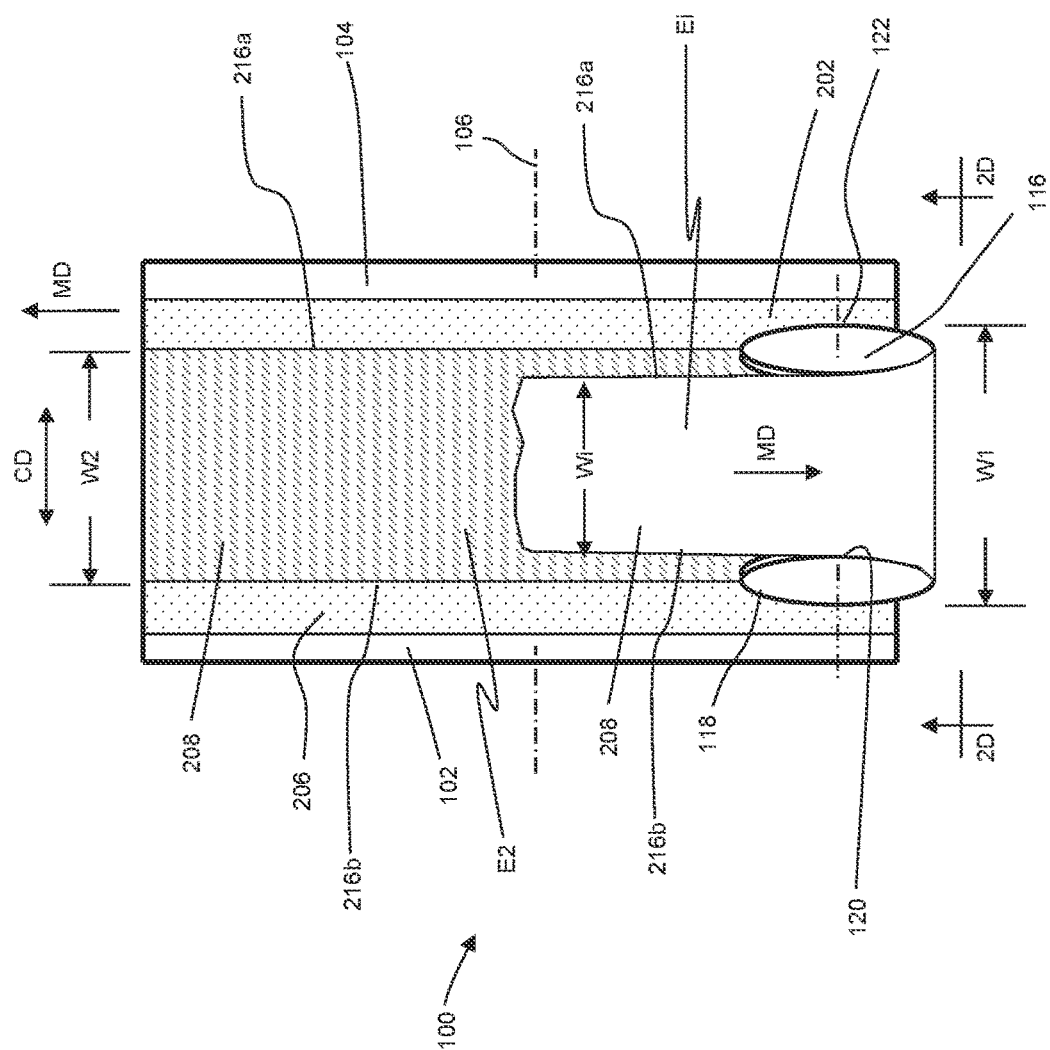
FIG. 2B is a left side view of the apparatus from FIG. 2A taken along line 2B-2B.

As shown in FIGS. 2A-2C, a first substrate 202 advances in a machine direction MD onto the rotating anvil 102. More particularly, the first substrate 202 includes a first surface 204 and an opposing second surface 206, and the first substrate 202 advances to wrap the first surface 204 onto the outer circumferential surface 104 of the rotating anvil 102. During the assembly process, the spreader mechanism 112 activates an elastic material 208 by stretching the elastic material 208 to a first elongation in the cross direction CD. The stretched elastic material 208 is then consolidated to a second elongation that is less than the first elongation. And the consolidated elastic material 208 is positioned into contact with the second surface 206 of the first substrate 202. As discussed in more detail below, the stretched elastic material 208 may be consolidated before advancing to the anvil 102, and in some configurations, the elastic material 208 may be consolidated after advancing to the anvil 102. In turn, the elastic laminate 200 may be formed by ultrasonically bonding the first substrate 202 and the elastic material 208 together with a second substrate 210 on the anvil 102. More particularly, the second substrate 210 includes a first surface 212 and an opposing second surface 214, and the second substrate 210 advances to position the first surface 212 in contact with the elastic material 208 and the second surface 206 of the first substrate 202.

With continued reference to FIGS. 2A-2C, as the anvil 102 rotates, the first substrate 202, the elastic material 208, and the second substrate 210 are advanced between the outer circumferential surface 104 of the anvil 102 and the ultrasonic horn 132. In turn, the ultrasonic horn 132 bonds the first substrate 204, the elastic material 208, and the second substrate 210 together to form the elastic laminate 200. As shown in FIGS. 2A and 2E, the elastic laminate 200 may then advance from the anvil 102 to additional absorbent article assembly processes. FIG. 2F also shows the elastic laminate 200 in a relaxed state wherein the central region 208c of the elastic material 208 is contracted in the cross direction CD. During the ultrasonic bonding process, it is to be appreciated that bonds imparted into the elastic laminate 200 from the ultrasonic horn 132 may correspond with patterns and/or shapes defined by the plurality of pattern elements 134 extending radially outward from the outer circumferential surface 104 of the anvil 102. It is to be appreciated that the elastic laminate 200 may include various portions of components bonded together in various ways and with differing or identical bond patterns. For example, the elastic material 208 may be bonded together with the first and/or second substrates 202, 210, and the first substrate 202 may be bonded directly to the second substrate 210 in areas of the elastic laminate 200. It is to be appreciated that the apparatus 100 may be adapted to create various types of bond configurations, such as disclosed, for example, in U.S. Pat. No. 6,572,595.

As previously mentioned, the spreader mechanism 112 activates the elastic material 208 by stretching the elastic material 208 to a first elongation in the cross direction CD. With particular reference to FIGS. 2A and 2D, the elastic material 208 includes a first edge 216a and a second edge 216b separated from the first edge 216a in the cross direction CD. In addition, the elastic material 208 includes a first edge region 208a adjacent the first edge 216a and a second edge region 208b adjacent the second edge 216b. The first edge region 208a is separated from the second edge region 208b in the cross direction CD by a central region 208c. As shown in FIGS. 2A and 2B, the elastic material 208 may define an initial width Wi in the cross direction CD between the first edge 216a and the second edge 216b upstream of the spreader mechanism 112. The elastic material 112 advances in a machine direction MD onto the spreader mechanism 112 at or downstream of the first location 120. It is to be appreciated that elastic material 208 may be at the initial width Wi in the cross direction CD while advancing onto the spreader mechanism 112. It is also to be appreciated that the elastic material 206 may be in a relaxed state upstream of the spreader mechanism 112.

As shown in FIGS. 2B and 2D, the first edge region 208a of the elastic material 208 advances onto the outer rim 116b of the first disk 116 of the spreader mechanism 112, and the second edge region 208b advances onto the outer rim 118b of the second disk 118. As previously discussed with reference to FIG. 1D, the outer rims 116b, 118b of the first and second disks 116, 118 of the spreader mechanism 112 may include channels 124 fluidly connected to a vacuum pressure source 129 and may include radially protruding nubs 128. Thus, as shown in FIG. 2D, the first edge region 208a of the elastic material 208 may be held in position on the outer rim 116b with vacuum air pressure in the channels 124 and with the radially protruding nubs 128. Similarly, the second edge region 208b of the elastic material 208 may be held in position on the outer rim 118b with vacuum air pressure in the channels 124 and with the radially protruding nubs 128.

As discussed above with reference to FIG. 1D, the first disk 116 and the second disk 118 are canted. Thus, as the first disk 116 and the second disk 118 of the spreader mechanism 112 rotate, the elastic material 208 is stretched in the cross direction CD while advancing from the first location 120 or downstream of the first location 120 toward the second location 122. Thus, as shown in the FIGS. 2A, 2B, and 2D, the spreader mechanism 112 may activate the elastic material 208 by stretching the elastic material 208 in the cross direction CD from the initial width Wi (and an initial elongation Ei) to a first width W1 (and a first elongation E1) in the cross direction CD, wherein W1 is greater than Wi and wherein E1 is greater than Ei.

As the first disk 116 and the second disk 118 continue to rotate in direction Dir2 and advance the elastic material 208 past the second location 122, the spreader mechanism 112 consolidates the elastic material 208 to a second width W2 (and second elongation E2), wherein W2 is less than W1 and wherein E2 is less than E1. It is to be appreciated that the elastic material 208 remains stretched at the second width W2 (and second elongation E2). It is also to be appreciated that the elastic material 208 may be in a relaxed state at the initial width Wi (and initial elongation Ei), and as such, the second width W2 may be greater than the initial width Wi and the second elongation E2 may be greater than the initial elongation Ei.

It is to be appreciated that the apparatuses 100 herein may be configured to operate with various extensions of elastic material. In some configurations, the difference between the first elongation E1 and the second elongation E2 may be about 25%. In some configurations, E1−E2=25%. In some configurations, when the spreader mechanism includes canted disks, the first and second edge regions 208a, 208b of the elastic material 208 may be held in position on the outer rims 116b, 118b of the disks 116, 118. And as such, some portions of the first and second edge regions 208a, 208b may remain unstretched in the cross direction CD as the first and second disks 116, 118 rotate. Thus, as the first disk 116 and the second disk 118 of the first spreader mechanism 112 rotate, the central region 208c of the elastic material 208 is stretched in the cross direction CD. In some configurations, the initial elongation Ei of the central region 208c may be zero percent; the first elongation E1 may be about 225%, and the second elongation may be about 180%.

As shown in FIG. 2A-2D, the consolidated elastic material 208 advances from the spreader mechanism 112 downstream of the second location 122 to the anvil 102, and onto the second surface 206 of the first substrate 202 on the anvil 102. And as the anvil 102 rotates, the second substrate 210 advances onto anvil 102 to position the first surface 212 in contact with elastic material 208 and the second surface 206 of the first substrate 202 to form an elastic laminate 202 wherein the first substrate 202, elastic material 208, and second substrate 210 are bonded together.

Figure 2G:
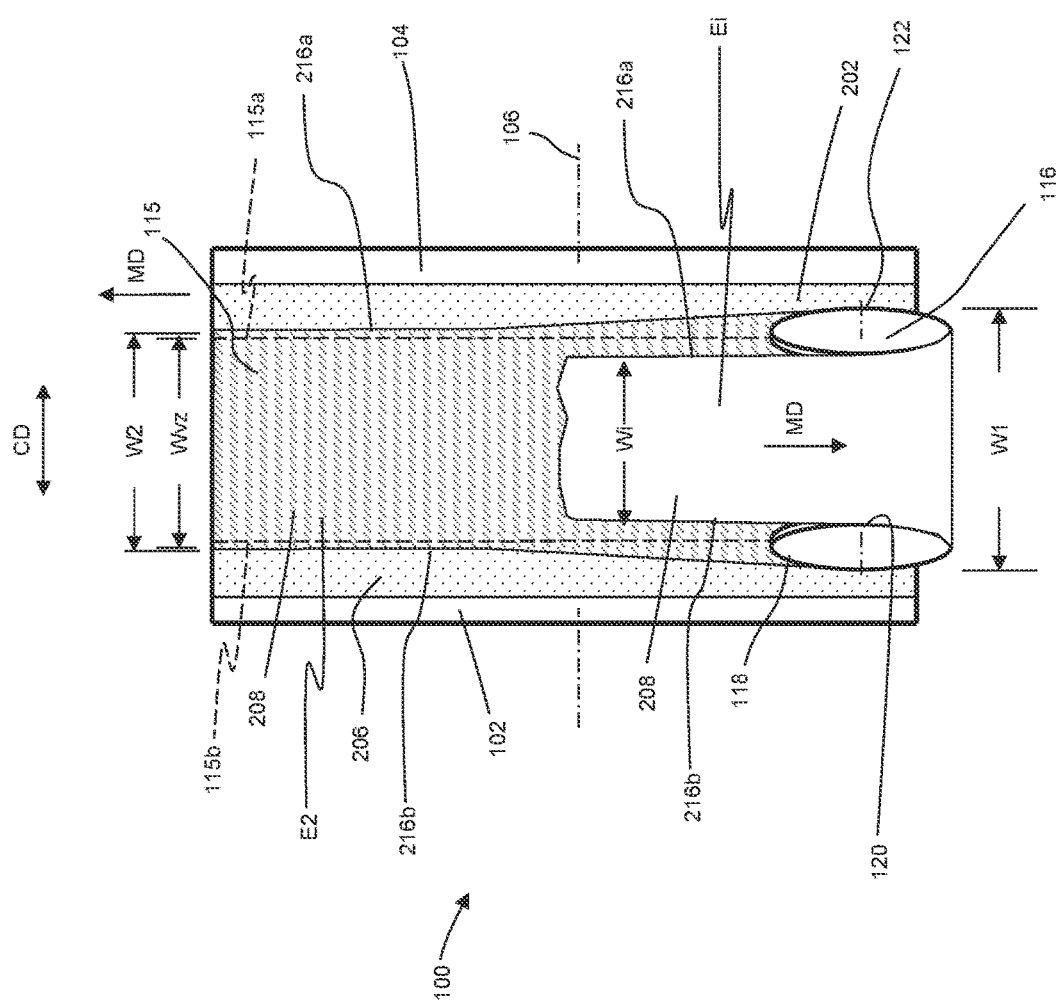
FIG. 2G is a left side view of the apparatus illustrating elastic material being consolidated on the anvil.

Although the spreader mechanism 112 can be configured to activate and consolidate the elastic material 208 before advancing to the anvil 102, it is to be appreciated that in some configurations, the elastic material 208 may be consolidated after advancing from the spreader mechanism 112 to the anvil 102. For example, as shown in FIG. 2G, the elastic material 208 advances in a machine direction MD onto the spreader mechanism 112 at or downstream of the first location 120. And the spreader mechanism 112 may activate the elastic material 208 by stretching the elastic material 208 in the cross direction CD from the initial width Wi (and an initial elongation Ei) to a first width W1 (and a first elongation E1) in the cross direction CD, wherein W1 is greater than Wi and wherein E1 is greater than Ei. Once the elastic material 208 advances to the second location 122 or before the elastic material advances to the second location 122 on the spreader mechanism 112, the stretched elastic material 208 having the first width W1 (and first elongation E1) advances onto the anvil 102. As such, the elastic material 208 may be removed from the spreader mechanism 112 at or upstream of the second location 122.

As previously mentioned, the outer circumferential surface 104 of the anvil 102 may be fluidly connected with the vacuum source 105, and as such, vacuum air pressure may be applied to the first substrate 202 on the anvil 102. In addition, when the first substrate 202 is configured as a porous substrate, such as a nonwoven, vacuum air pressure may also be applied to the elastic material 208 on the anvil 102, and as such, may help maintain the stretched condition of the of the elastic material 208 while on the anvil 102. As further discussed above with reference to FIG. 1G, the outer circumferential surface 104 of the anvil roll 102 may include a plurality of apertures 114 fluidly connected with the vacuum pressure source 105. In turn, the vacuum zone 115 defined by the apertures 114 extends axially or in the cross direction CD for a width, Wvz. As such, the vacuum pressure exerted on the elastic material 208 while on the anvil 102 may maintain the width of the elastic material 208 at a width that is equal to or about equal to the width Wvz of the vacuum zone 115. In some configurations, the width Wvz of the vacuum zone 115 may be less than the first width W1 of the elastic material 208 advancing from the spreader mechanism 112. Thus, as shown in FIG. 2G, the elastic material 208 advancing to the anvil roll 102 from the spreader mechanism 112 may be consolidated to a second width W2 (and second elongation E2) as defined by the width Wvz of the vacuum zone 115, wherein W2 and Wvz are both less than W1 and wherein E2 is less than E1. It is also to be appreciated that the elastic material 208 may be consolidated to the second width W2 (and second elongation E2) while advancing from the spreader mechanism 112 to the anvil 102. It is also to be appreciated that the elastic material 112 may be partially consolidated while on the spreader mechanism 112 and while on the anvil 102.

It is also to be appreciated that aspects of the spreader mechanisms 112 may be configured in various ways. For example, the cross direction CD positions of the disks 116, 118 of the spreader mechanism 112 may be adjustable relative to each other. In addition, canting angles of the disks 116, 118 of the spreader mechanism 112 may be adjustable. The canting angle of the first disk 116 may be defined as an angular offset between the axis of rotation 116a of the first disk 116 and the axis of rotation 106 of the anvil 102, and the canting angle of the second disk 118 may be defined as an angular offset between the axis of rotation 118a of the second disk 118 and the axis of rotation 106 of the anvil 102. In some configurations, radial clearances between the outer circumferential surface 104 of the anvil 102 and the outer rims 116b, 118b of the first and second disks 116, 118 of the spreader mechanisms 112 may be adjustable, wherein the positions of the disks 116, 118 may be configured to be independently or collectively adjustable. In some configurations, the radial clearance between the outer circumferential surface 104 of the anvil 102 and the outer rims 116b, 118b may be zero or greater than zero.

It is to be appreciated that various drives may be used to control the rotation of the disks 116, 118 of the spreader mechanism 112. For example, the disks 116, 118 of the spreader mechanism 112 may be driven by one or more motors, such as a servo motor. In some configurations, motors may be directly connected with the disks 116, 118, and in some configurations, motors may be indirectly connected with the disks 116, 118, such as through belts, pulleys, and/or gears. The disks 116, 118 may be driven as a pair through the use of a common driveshaft with a coupling between the disks. In some configurations, a common jackshaft may be used to drive both disks 116, 118 together with a single motor. In some configurations, drives of the anvil 102 and spreader mechanism 112 may be operatively connected, and may be configured with a single motor. In some configurations, the disks 116, 118 of the spreader mechanism 112 may be driven only by the advancement of the elastic material 208. In some configurations, the disks 116, 118 of the spreader mechanism 112 may be driven by rotation of the anvil 102 or an infeed idler. Other drives may include surface driving through a jackshaft with a friction material in operative contact with disks 116, 118.

Figure 3A:
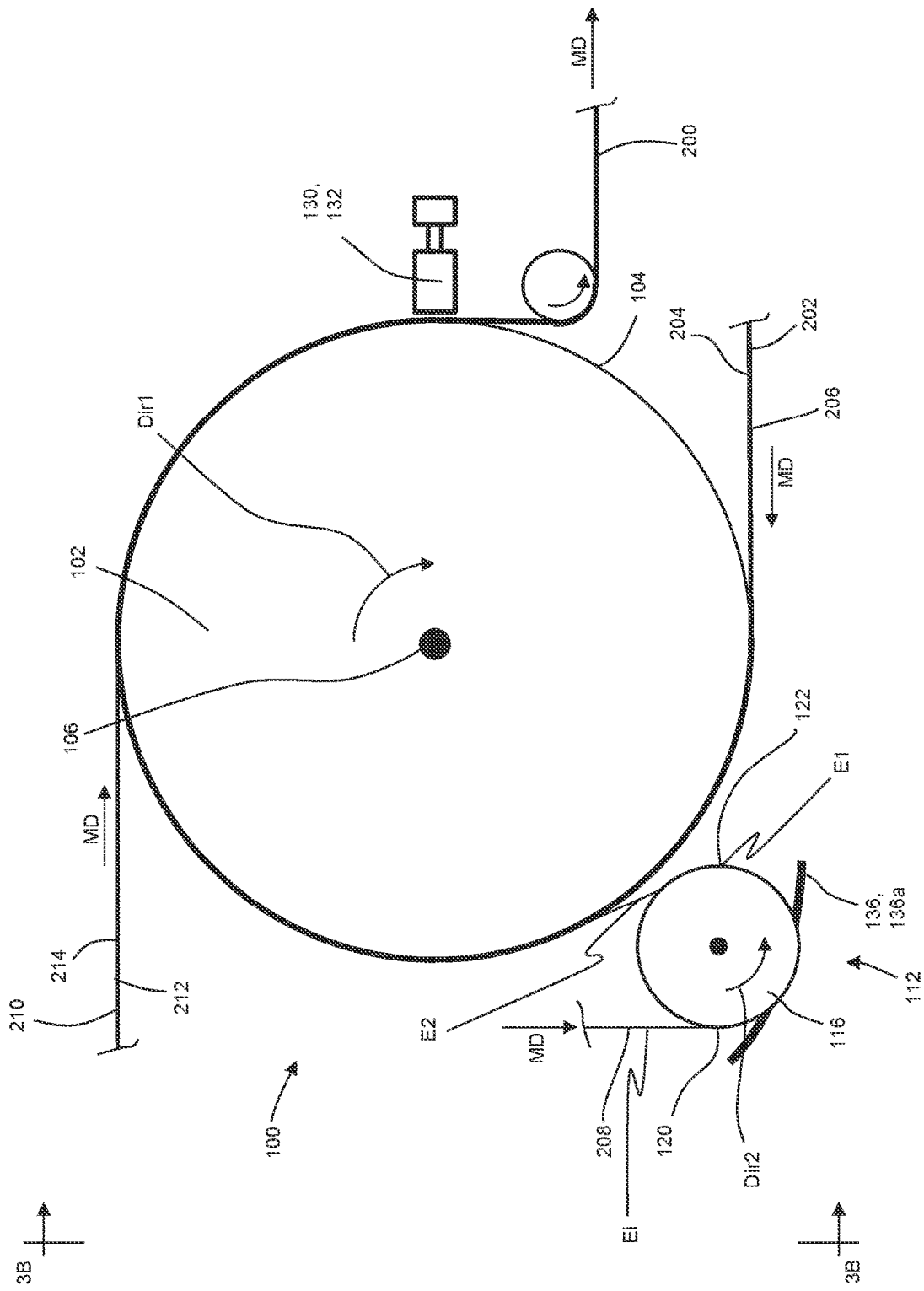
FIG. 3A is a schematic side view of a second apparatus operating to assemble elastic laminates including a deflection member in the form of an elongate member positioned between the first disk and the second disk of the spreader mechanism.
Figure 3B:
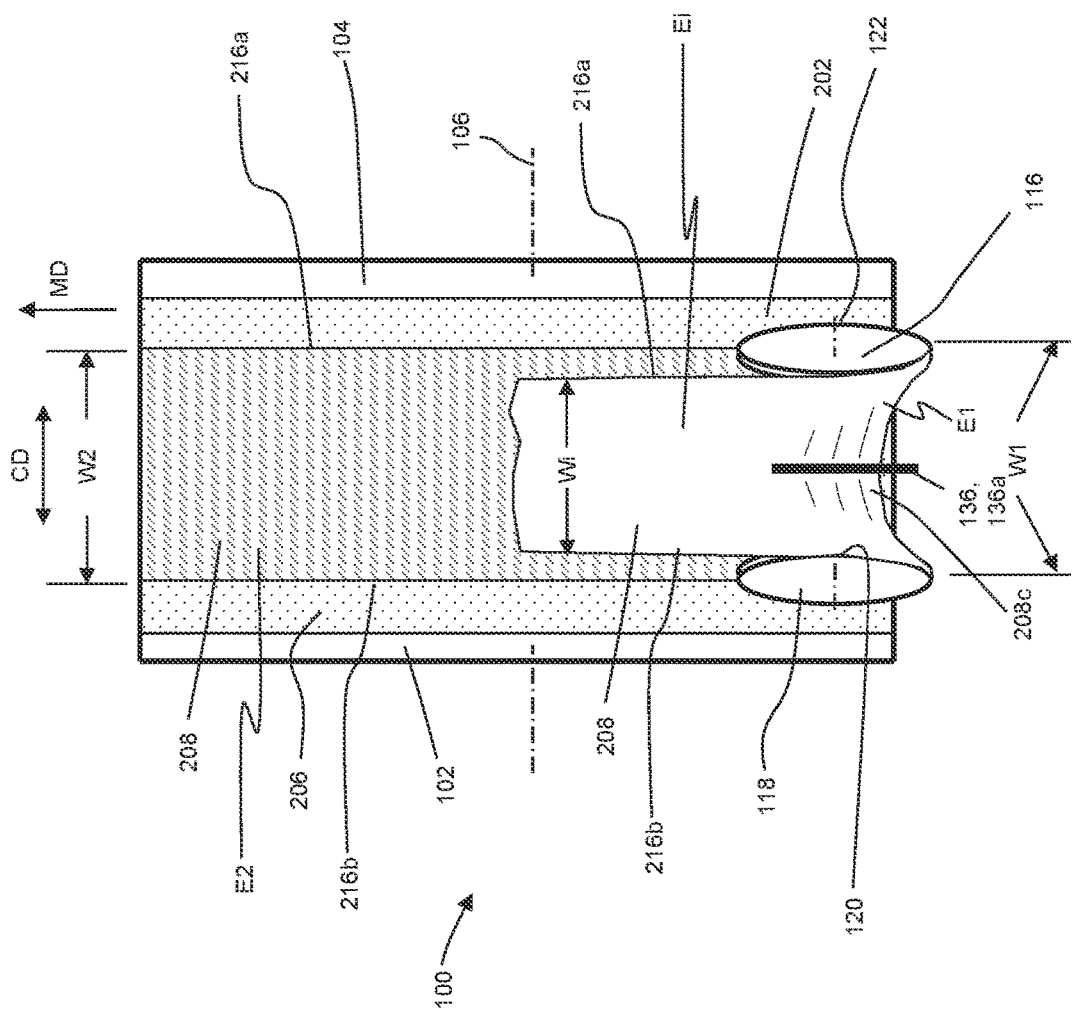
FIG. 3B is a left side view of the apparatus from FIG. 3A taken along line 3B-3B.

It is to be appreciated that the spreader mechanism 112 may be configured to activate the elastic material 208 in various ways. For example, as shown in FIGS. 3A and 3B, the spreader mechanism 112 may include a deflection member 136 positioned between the first disk 116 and the second disk 118. During operation, the central region 208c the elastic material 208 may advance along the deflection member 136 as the first disk 116 and the second disk 118 rotate. In turn, the deflection member 136 deflects the central region 208c of the elastic material into the space between the first disk 116 and the second disk 118. The deflection imparted by the deflection member 136 onto the elastic material 208 causes the elastic material 208 to stretch. As such, the stretching caused by the deflection member 136 may be configured to impart stretch that is in addition to the stretch caused by the canted relationship of the first disk 116 and the second disk 118.

Figure 3C:
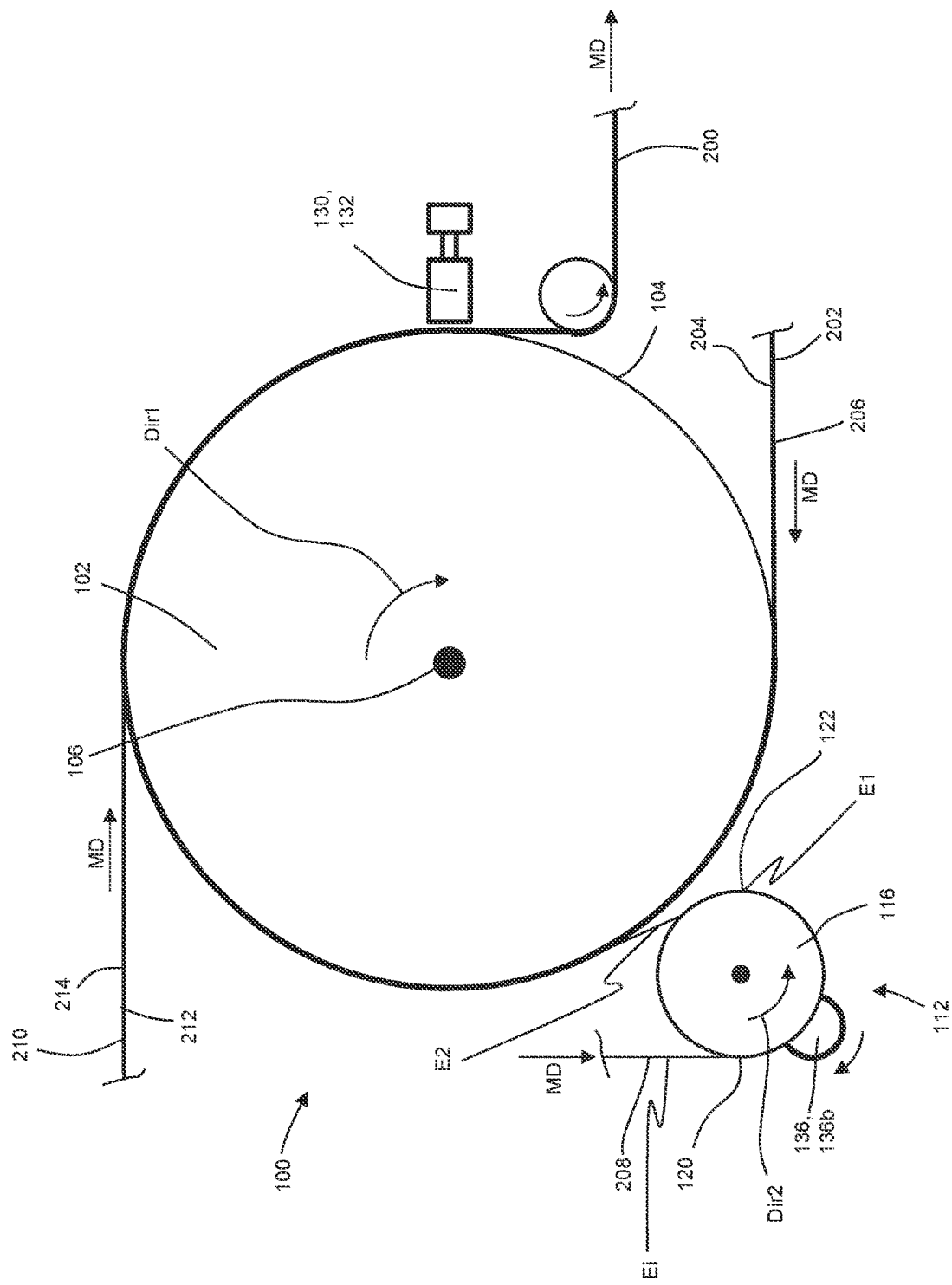
FIG. 3C is a schematic side view of the second apparatus operating to assemble elastic laminates including a deflection member in the form of a rotating disk positioned between the first disk and the second disk of the spreader mechanism.

It is to be appreciated that the deflection member 136 may be configured in various ways. For example, the deflection member 136 is illustrated in FIGS. 3A and 3B as an elongate member 136a extending in the machine direction MD between the first disk 116 and the second disk 118. In another example, such as shown in FIG. 3C, the member may be configured as a rotating disk 136b positioned between the first disk 116 and the second disk 118. In some configurations, the deflection member 136 may be configured with a pneumatic device so as to discharge air onto the elastic material 208. In some configurations, the elastic material 208 may be supported on a layer of compressed air from the deflection member 136. In some configurations, the position and/or geometry of the deflection member 136 may be adjustable, which in turn, may allow for regulation of the first width W1 (and first elongation E1). It is to be appreciated that the deflection member 136 may be arranged and/or configured with respect to the disks 116, 118 such that the first disk 116 and the second disk 118 may be parallel with respect to each other, as opposed to being canted. It is also to be appreciated that the deflection member 136 may be arranged and/or configured with respect to the disks 116, 118 such that the elastic material 208 may be consolidated before or after advancing to the second location 122. It is also to be appreciated that the deflection member 136 may be configured with curved and/or straight regions, and may be configured to deflect the elastic material 208 outward from between the disks 116, 118. As discussed above, once activated, the stretched elastic material 208 may be then be consolidated on the spreader mechanism 112 shown in FIGS. 3A and 3B and/or may be consolidated on the anvil 102.

Figure 4:
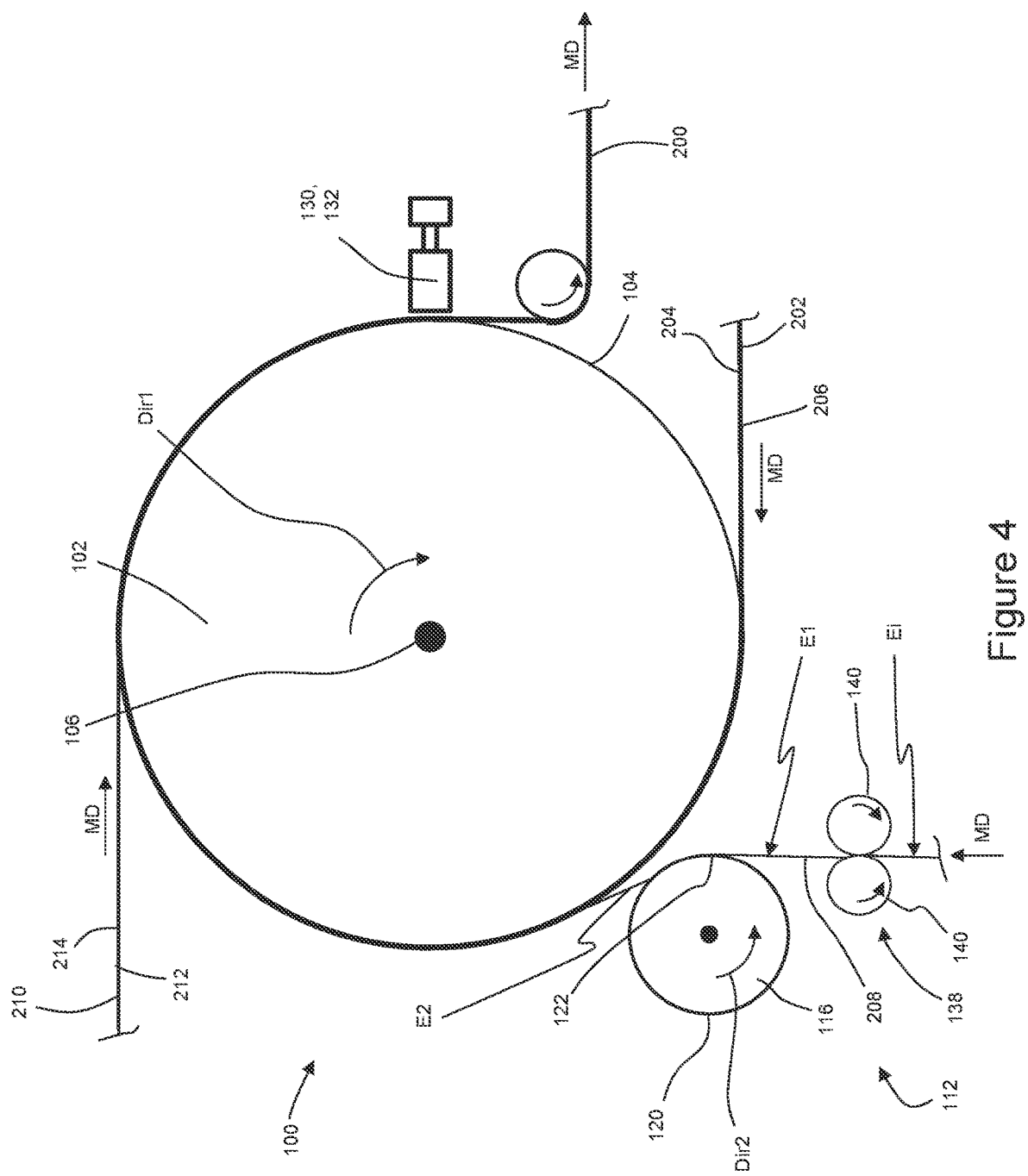
FIG. 4 is a schematic side view of a third apparatus operating to assemble elastic laminates.
Figure 4A:
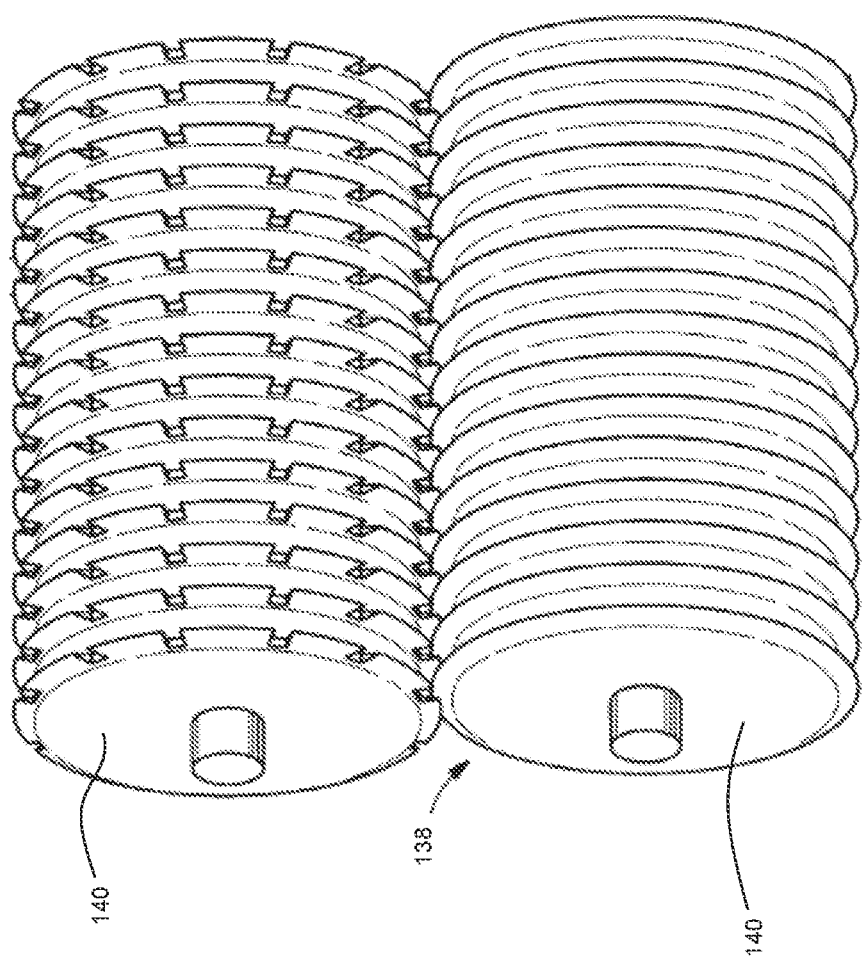
FIG. 4A is an isometric view of a ring rolling apparatus.

As shown in FIG. 4, the spreader mechanism 112 may include a ring rolling apparatus 138, such as disclosed for example in U.S. Pat. Nos. 4,116,892; 4,834,741; 5,143,679; 5,156,793; 5,167,897; 5,422,172; and 5,518,801; and 9,687, 580. In some configurations, the ring rolling apparatus 138 may include two profile rollers 140, such as shown for example in FIG. 4A. It is to be appreciated that the rollers 140 such as shown in FIG. 4A may also be configured to be duplicate to each other. Each roller 140 may include at least two disk packets having a plurality of intermeshing disks that are situated on an axis. Referring back to FIG. 4, the elastic material 208 may advance through a nip between the two profile rollers 140, and in turn, the ring rolling apparatus 138 activates the elastic material 208 by stretching the elastic material 208 in the cross direction CD from the initial width Wi (and an initial elongation Ei) to a first width W1 (and a first elongation E1) in the cross direction CD, wherein W1 is greater than Wi and wherein E1 is greater than Ei. The activated elastic material 208 may then advance to the first disk 116 and the second disk 118 at or downstream of the second location 122. As the first and second disks 116, 118 rotate and advance the elastic material 208 downstream of the second location 122, the elastic material 208 is consolidated to a second width W2 (and second elongation E2), wherein W2 is less than W1 and wherein E2 is less than E1. The consolidated elastic material 208 then advances from the first disk 116 and the second disk 118 and onto the anvil 102. It is also to be appreciated that the apparatus 100 shown in FIG. 4 may be modified to eliminate the first disk 116 and the second disk 118, and as such, the activated elastic material 208 may advance directly to the anvil 102 from the ring rolling apparatus 138. As such, the elastic material 208 may be consolidated to the second width W2 (and second elongation E2) while advancing from the ring rolling apparatus 138 to the anvil 102 and/or may be consolidated while on the anvil 102 as discussed above.

It is to be appreciated that the apparatus 100 herein may be configured to activate the elastic material 208, in various ways. For example, the apparatus 100 may be configured to create zones in components of the elastic material 208 that have different stretch properties, tactile differences, and/or aesthetic differences, such as disclosed in U.S. Pat. No. 8,118,801 and U.S. Patent Publication No. US20120143165A1. In some configurations, the apparatus 100 may be configured to activate the elastic material 208 in the machine direction MD and/or the cross direction CD, such as disclosed in U.S. Pat. Nos. 7,824,594; 7,896,641; and 8,062,572.

It is to be appreciated that aspects of the apparatus 100 herein may be configured to assemble elastic laminates from various types of material and/or components. For example, it is to be appreciated that the first substrate 202 and/or the second substrate 210 discussed above may be configured as the same or different types of materials. For example, the substrates 202, 210 may be configured as single layer or multi-layer nonwovens. As previously mentioned the elastic material 208 may be configured in various ways and from various materials. For example, the elastic material may be formed by any suitable method in the art, for example, by extruding molten thermoplastic and/or elastomeric polymers or polymer blends through a slit die and subsequently cooling the extruded sheet. Other non-limiting examples for making film forms include casting, blowing, solution casting, calendaring, and formation from aqueous or, non-aqueous cast dispersions. The elastomer composition may be made into a film having a basis weight of from about 5 to about 150 g/m$^2$. The elastic material can also be an apertured film made of elastomeric material to provide breathability. In some configurations, the elastic material include a nonwoven web of synthetic fibers. The web can be made of fibers from elastomers or can be mixture of elastomeric fibers with plastic fibers. The elastic material may also be configured as laminates including elastic material connected with and/or interposed between an outer layer and an inner layer. The elastic material may include one or more elastic elements such as strands, ribbons, or panels. Suitable elastomeric compositions for making elastic materials comprise thermoplastic elastomers selected from the group consisting of styrenic block copolymers, poly-esters, polyurethanes, polyether amides, polyolefin elastomers, and combinations thereof.

Although the apparatus 100 may be configured to operate online as part of an absorbent article assembly process, it is to be appreciated that aspects of the apparatus 100 herein may be configured in various ways and may operate to assemble elastic laminates 200 from various types of material and/or components. For example, it is to be appreciated that in some configurations, the elastic laminate assembly operations may be performed separate to a final assembly process, such as for example, assembling the elastic laminates offline wherein the elastic laminates may be stored until needed for production. For example, elastic laminate assembly operations may be accomplished on discrete assembly lines, separately from converting lines that may be dedicated to manufacturing disposable absorbent articles. After assemblage on the discrete lines, the elastic laminates may be delivered to the absorbent article converting lines, such as in a form of rolls of continuous elastic laminates. It is to be appreciated that such rolls of continuous elastic laminates may be planetary wound or traversely wound. It is also appreciated that the elastic laminate assembly process may be done online during the article assembly process.

It is also to be appreciated that the features illustrated or described in connection with one non-limiting configuration may be combined with the features of other non-limiting configurations. Such modifications and variations are intended to be included within the scope of the present disclosure.

Figure 5B:
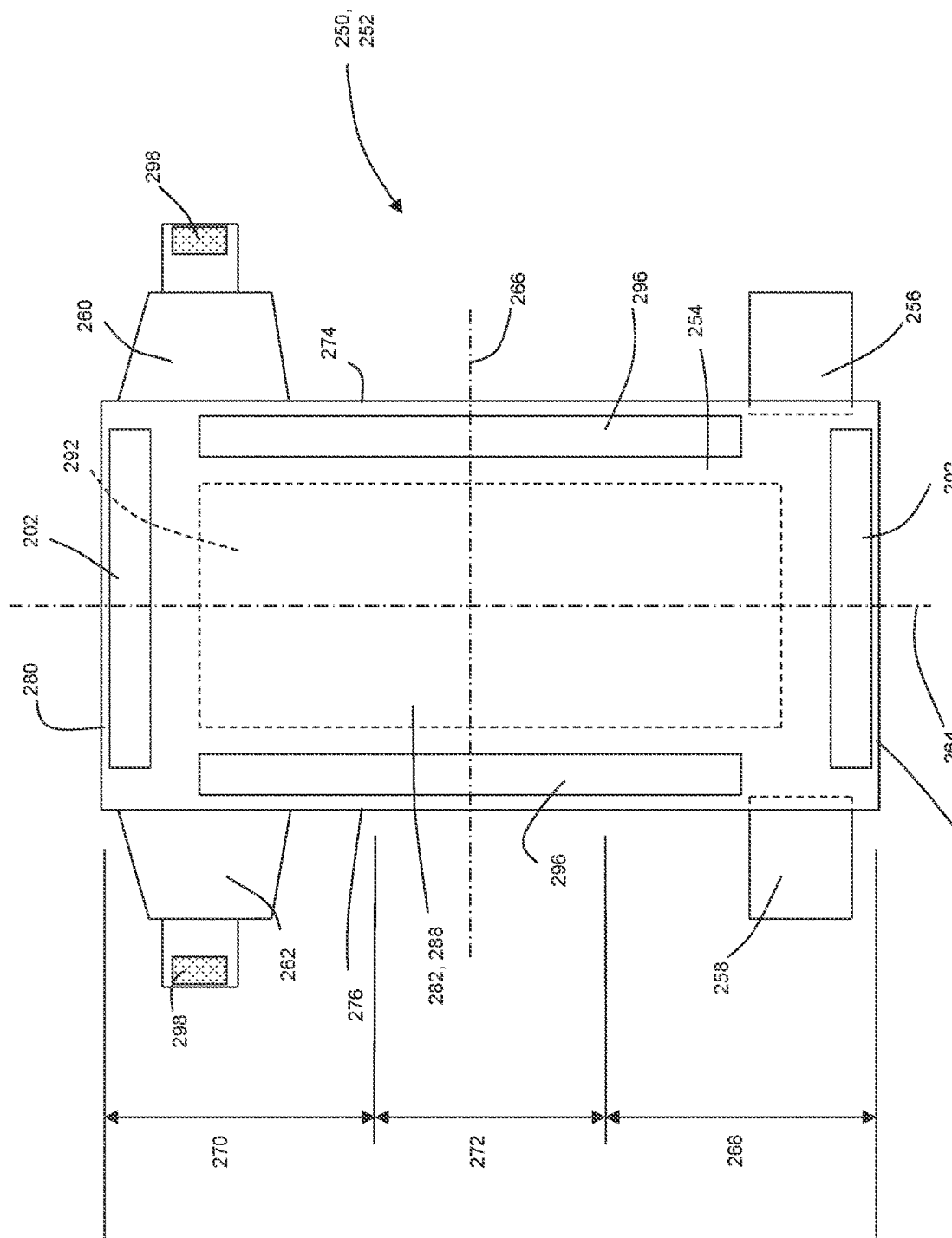
FIG. 5B is a plan view of the absorbent article of FIG. 5A that may include one or more elastic laminates manipulated during manufacture according to the apparatuses and methods disclosed herein with the portion of the diaper that faces toward a wearer oriented towards the viewer.

As mentioned above, apparatuses and methods of the present disclosure may be utilized to assembly various forms of elastic laminates used in the manufacture of absorbent articles. Such elastic laminates may be utilized in absorbent article components such as, for example: backsheets, topsheets, absorbent cores, front and/or back ears, fastener components, and various types of elastic webs and components such as leg elastics, barrier leg cuff elastics, and waist elastics. For the purposes of a specific illustration, FIGS. 5A and 5B show an example of a disposable absorbent article 250 in the form of a diaper 252 that may be constructed from such elastic laminates manipulated during manufacture according to the apparatuses and methods disclosed herein. In particular, FIG. 5A is a partially cut away plan view of an absorbent article in the form of a taped diaper that may include one or more elastic laminates assembled during manufacture according to the apparatuses and methods disclosed herein with the portion of the diaper that faces away from a wearer oriented towards the viewer. FIG. 5B is a plan view of the absorbent article of FIG. 5A that may include one or more elastic laminates assembled during manufacture according to the apparatuses and methods disclosed herein with the portion of the diaper that faces toward a wearer oriented towards the viewer.

As shown in FIGS. 5A and 5B, the diaper 252 includes a chassis 254 having a first ear 256, a second ear 258, a third ear 260, and a fourth ear 262. To provide a frame of reference for the present discussion, the chassis is shown with a longitudinal axis 264 and a lateral axis 266. The chassis 254 is shown as having a first waist region 268, a second waist region 270, and a crotch region 272 disposed intermediate the first and second waist regions. The periphery of the diaper is defined by a pair of longitudinally extending side edges 274, 276; a first outer edge 278 extending laterally adjacent the first waist region 268; and a second outer edge 280 extending laterally adjacent the second waist region 270. As shown in FIGS. 5A and 5B, the chassis 254 includes an inner, body-facing surface 282, and an outer, garment-facing surface 284. A portion of the chassis structure is cut-away in FIG. 5A to more clearly show the construction of and various features that may be included in the diaper. As shown in FIGS. 5A and 5B, the chassis 254 of the diaper 252 may include a topsheet 288 defining the inner, body-facing surface 282, and a backsheet 290 defining the outer, garment-facing surface 284. An absorbent core 292 may be disposed between a portion of the topsheet 288 and the backsheet 290. As discussed in more detail below, any one or more of the regions may be stretchable and may include an elastomeric material or laminate as described herein. As such, the diaper 252 may be configured to adapt to a specific wearer's anatomy upon application and to maintain coordination with the wearer's anatomy during wear.

The absorbent article 250 may also include an elastic waist feature 202 shown in FIG. 5B in the form of a waist band and may provide improved fit and waste containment. The elastic waist feature 202 may be configured to elastically expand and contract to dynamically fit the wearer's waist. The elastic waist feature 202 can be incorporated into the diaper and may extend at least longitudinally outwardly from the absorbent core 292 and generally form at least a portion of the first and/or second outer edges 278, 280 of the diaper 252. In addition, the elastic waist feature may extend laterally to include the ears. While the elastic waist feature 202 or any constituent elements thereof may comprise one or more separate elements affixed to the diaper, the elastic waist feature may be constructed as an extension of other elements of the diaper, such as the backsheet 290, the topsheet 288, or both the backsheet and the topsheet. In addition, the elastic waist feature 202 may be disposed on the outer, garment-facing surface 284 of the chassis 254; the inner, body-facing surface 282; or between the inner and outer facing surfaces. The elastic waist feature 202 may be constructed in a number of different configurations including those described in U.S. Patent Publication Nos. 2007/0142806 A1; 2007/0142798 A1; and 2007/0287983 A1, all of which are hereby incorporated by reference herein.

As shown in FIGS. 5A and 5B, the diaper 252 may include leg cuffs 296 that may provide improved containment of liquids and other body exudates. In particular, elastic gasketing leg cuffs can provide a sealing effect around the wearer's thighs to prevent leakage. It is to be appreciated that when the diaper is worn, the leg cuffs may be placed in contact with the wearer's thighs, and the extent of that contact and contact pressure may be determined in part by the orientation of diaper on the body of the wearer. The leg cuffs 296 may be disposed in various ways on the diaper 202.

The diaper 252 may be provided in the form of a pant-type diaper or may alternatively be provided with a re-closable fastening system, which may include fastener elements in various locations to help secure the diaper in position on the wearer. For example, fastener elements 298 may be located on the ears and may be adapted to releasably connect with one or more corresponding fastening elements located in the first or second waist regions. For example, as shown in FIG. 5A, the diaper 252 may include a connection zone 282, sometimes referred to as a landing zone, in the first waist region 268. It is to be appreciated that various types of fastening elements may be used with the diaper.

EXAMPLES

A. A method for assembling elastic laminates, the method comprising the steps of: providing a first substrate and a second substrate, the first substrate and the second substrate each comprising a first surface and an opposing second surface, and defining a width in a cross direction; wrapping the first surface of the first substrate onto an outer circumferential surface of an anvil; advancing an elastic film to a spreader mechanism, the elastic film comprising a first edge and a second edge separated from the first edge in the cross direction by a central region; stretching the elastic film at the spreader mechanism in the cross direction to a first elongation; advancing the elastic film from the spreader mechanism to the anvil; consolidating the elastic film to a second elongation in the cross direction, wherein the second elongation is less than the first elongation; positioning the consolidated elastic film in contact with the second surface of the first substrate on the anvil; advancing the second substrate to position the first surface of the second substrate in contact with the consolidated elastic film and the second surface of the first substrate on the anvil; and ultrasonically bonding the first substrate together with the second substrate with the elastic film positioned between the first substrate and the second substrate.

B. The method according to paragraph A, wherein the spreader mechanism comprises a first disk and a second disk canted relative each other, each disk comprising an outer rim, wherein as the first and second disks rotate, the outer rims are separated from each other by a distance that increases from a minimum distance at a first location to a maximum distance at a second location.

C. The method according to paragraph B, further comprising the steps of: advancing the elastic film onto the first disk and the second disk at or downstream of the first location; stretching the elastic film to the first elongation in the cross direction by rotating the first disk and the second disk of the spreader mechanism.

D. The method according to paragraph C, wherein the step of consolidation further comprises: advancing the elastic film on the rotating first disk and second disk downstream of the second location.

E. The method according to paragraph D, further comprising the step of removing the elastic film from the first disk and the second disk downstream of the second location and advancing the elastic film from the spreader mechanism to the anvil.

F. The method according to paragraph C, wherein the step of stretching the elastic film further comprises advancing the central region of the elastic film along a deflection member positioned between the first disk and the second disk.

G. The method according to paragraph F, wherein the deflection member comprises a rotating disk.

H. The method according to paragraph A, wherein the spreader mechanism comprises a ring rolling apparatus.

I. The method according to paragraph H, further comprising the step of advancing the elastic film from the ring rolling apparatus to a first disk and a second disk, wherein the first disk and the second disk are canted relative each other, each disk comprising an outer rim, wherein as the first and second disks rotate, the outer rims are separated from each other by a distance that increases from a minimum distance at a first location to a maximum distance at a second location.

J. The method according to paragraph I, wherein the step of consolidating further comprises: advancing the elastic film on the rotating first disk and second disk downstream of the second location.

K. A method for assembling elastic laminates, the method comprising the steps of: providing a first substrate and a second substrate, the first substrate and the second substrate each comprising a first surface and an opposing second surface, and defining a width in a cross direction; wrapping the first surface of the first substrate onto an outer circumferential surface of an anvil; advancing an elastic film to a spreader mechanism, the elastic film comprising a first edge and a second edge separated from the first edge in the cross direction by a central region; activating the elastic film by stretching the elastic film at the spreader mechanism in the cross direction to a first elongation; advancing the elastic film from the spreader mechanism to the anvil; positioning the elastic film in contact with the second surface of the first substrate on the anvil; consolidating the elastic film on the anvil to a second elongation in the cross direction, wherein the second the elongation is less than the first elongation; advancing the second substrate to position the first surface of the second substrate in contact with the elastic film and the second surface of the first substrate on the anvil; and bonding the first substrate together with the second substrate with the elastic film in the second elongation positioned between the first substrate and the second substrate.

L. The method according to paragraph K, wherein the spreader mechanism comprises a first disk and a second disk canted relative each other, each disk comprising an outer rim, wherein as the first and second disks rotate, the outer rims are separated from each other by a distance that increases from a minimum distance at a first location to a maximum distance at a second location.

M. The method according to paragraph L, further comprising the steps of: advancing the elastic film onto the first disk and the second disk at or downstream of the first location; stretching the elastic film to the first elongation in the cross direction by rotating the first disk and the second disk.

N. The method according to paragraph M, further comprising the step of removing the elastic film from the first disk and the second disk at, upstream, or downstream of the second location and advancing the elastic film from the first disk and the second disk to the anvil.

O. The method according to paragraph L, wherein the step of stretching the elastic film further comprises advancing the central region of the elastic film along a deflection member positioned between the first disk and the second disk.

P. The method according to paragraph O, wherein the deflection member comprises a rotating disk.

Q. The method according to paragraph K, wherein the spreader mechanism comprises a ring rolling device.

R. The method according to any one of paragraphs K-Q, wherein the anvil comprises a vacuum zone comprising a width W extending in the cross direction, wherein the width W is less than the first elongation; and wherein the step of consolidating further comprises advancing the stretched elastic film from the spreader mechanism onto the vacuum zone.

S. The method according to any one of paragraphs K-Q, wherein the step of bonding further comprises advancing the first substrate, the second substrate, and the elastic film between the outer circumferential surface of the anvil and an ultrasonic horn.

T. An apparatus for making elastic laminates, the apparatus comprising: an anvil comprising an outer circumferential surface and adapted to rotate in a first direction about an axis of rotation, a plurality of pattern elements extending radially outward from the outer circumferential surface, the anvil extending axially from a first end to a second end in a cross direction; an ultrasonic horn adjacent the outer circumferential surface; a spreader mechanism upstream of the anvil in a machine direction and adapted to stretch an advancing elastic film in the cross direction to a first elongation; and a means for consolidating the stretched elastic film to a second elongation in the cross direction, wherein the second elongation is less than the first elongation.

This application claims the benefit of U.S. Provisional Application Nos. 62/374,010, filed on Aug. 12, 2016; 62/406,025, filed on Oct. 10, 2016; and 62/419,515, filed on Nov. 9, 2016, the entireties of which are all incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling elastic laminates, the method comprising steps of:
   providing a first substrate and a second substrate, the first substrate and the second substrate, each having a width in a cross direction and each having a first surface and an opposing second surface;
   providing an activated elastic material;
   elongating the activated elastic material using a spreader mechanism; and
   ultrasonically bonding the first substrate together with the second substrate with the elongated activated elastic material positioned between the first substrate and the second substrate.

2. The method of claim 1 wherein the step of elongating the activated elastic material comprises elongating the activated elastic material in a cross machine direction.

3. The method of claim 1 wherein the first substrate is a nonwoven.

4. The method of claim 3 wherein the seconds substrate is a nonwoven.

5. The method of claim 1 wherein the activated elastic material is an elastic film.

6. The method of claim 1 wherein the activated elastic material comprises a skin having a plurality of tears.

7. The method of claim 6 wherein the plurality of tears are formed by a ring rolling apparatus.

8. The method of claim 6 wherein the plurality of tears extend in a machine direction.

9. The method of claim 1 wherein the step of ultrasonically bonding the first substrate, second substrate and elongated activated elastic material comprises disposing the first substrate, second substrate, and elongated activated elastic material proximate to a plurality of pattern elements and applying ultrasonic energy to bond the substrates and activated elastic material to form discrete bonds in areas corresponding to the pattern elements.

10. The method of claim 1 wherein the elongated activated elastic material comprises an elongation that is greater than an elongation of the first and second substrates, such that the first and second substrates form gathers when the assembled elastic laminate is in a relaxed condition.

11. The method of claim 1 wherein the activated elastic material is capable of stretching to a first elongation and wherein the step of elongating the activated elastic material comprises elongating the activated elastic material to a second elongation, wherein the second elongation is less than the first elongation.

12. The method of claim 11 wherein the second elongation is about 25% less than the first elongation.

13. The method of claim 1 wherein the spreader mechanism comprises the first disk and the second disk are canted relative each other, wherein the first and second disks rotate.

14. The method of claim 1 further comprising the steps of:
   wrapping the first surface of the first substrate onto an outer circumferential surface of an anvil;
   positioning the activated elastic material in contact with the second surface of the first substrate on the anvil;
   advancing the second substrate to position the first surface of the second substrate in contact with the activated elastic material and the second surface of the first substrate on the anvil.

15. The method of claim 1 further comprising the step of using the spreader mechanism to hold one or more edge regions of the elastic material in position, such that the one or more edge regions remain unstretched.

16. The method of claim 1 further comprising the step of applying vacuum air pressure to the elastic material.

17. The method of claim 16 wherein an anvil comprises an vacuum source, and the step of applying vacuum air pressure comprises applying vacuum air pressure to the elastic material on the anvil.

18. A method for assembling elastic laminates, the method comprising steps of:
provxiding a first substrate and a second substrate, the first substrate and the second substrate, each having a width in a cross direction and each having a first surface and an opposing second surface;
providing an activated elastic film;
wrapping the first surface of the first substrate onto an outer circumferential surface of an anvil, wherein the anvil comprises a vacuum source;
positioning the activated elastic film in contact with the second surface of the first substrate on the anvil;
using the vacuum source to apply vacuum pressure to the elastic film while on the anvil to hold the activated elastic material in an elongated position;
advancing the second substrate to position the first surface of the second substrate in contact with the activated elastic film and the second surface of the first substrate on the anvil; and
ultrasonically bonding the first substrate together with the second substrate with the elongated activated elastic film positioned between the first substrate and the second substrate.

19. The method of claim 18 wherein the activated elastic film comprises a first edge region and a second edge region, and wherein the step of using a vacuum source to apply vacuum pressure to the elastic material comprises holding the first and/or second edge region in position, such such that said first and/or second edge region remains unstretched.

20. The method of claim 11 wherein the activated elastic film comprises a skin having a plurality of tears.

* * * * *